United States Patent
Vann et al.

(10) Patent No.: US 9,671,365 B2
(45) Date of Patent: *Jun. 6, 2017

(54) ELECTROWETTING DISPENSING DEVICES AND RELATED METHODS

(71) Applicant: Applied Biosystems, LLC, Carlsbad, CA (US)

(72) Inventors: Charles S. Vann, El Granada, CA (US); Debjyoti Banerjee, College Station, TX (US); Timothy G. Geiser, Petaluma, CA (US); James C. Nurse, Westport, WA (US); Nigel P. Beard, San Diego, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/817,573

(22) Filed: Aug. 4, 2015

(65) Prior Publication Data

US 2015/0338373 A1    Nov. 26, 2015

Related U.S. Application Data

(63) Continuation of application No. 14/479,824, filed on Sep. 8, 2014, now Pat. No. 9,132,400, which is a (Continued)

(51) Int. Cl.
*G01N 27/453* (2006.01)
*G01N 27/447* (2006.01)
(Continued)

(52) U.S. Cl.
CPC ........ *G01N 27/44743* (2013.01); *B01J 4/008* (2013.01); *B01L 3/0241* (2013.01);
(Continued)

(58) Field of Classification Search
CPC ....... B01L 2400/0427; B01L 3/502784; B01L 3/502792
See application file for complete search history.

(56) References Cited

U.S. PATENT DOCUMENTS

| 4,677,058 A | 6/1987 | Tryggvason et al. |
| 5,480,735 A | 1/1996 | Landsman et al. |

(Continued)

FOREIGN PATENT DOCUMENTS

| WO | 99/15876 | 4/1999 |
| WO | 03/069380 | 8/2003 |
| WO | 2004/027490 | 4/2004 |

OTHER PUBLICATIONS

Bellex International Corporation,"Bellex International Corporation product description of Cytop", Sep. 24, 2014.
(Continued)

*Primary Examiner* — Alexander Noguerola

(57) ABSTRACT

A method for dispensing liquid for use in biological analysis may comprise positioning liquid to be dispensed via electrowetting. The positioning may comprise aligning the liquid with a plurality of predetermined locations. The method may further comprise dispensing the aligned liquid from the plurality of predetermined locations through a plurality of openings respectively aligned with the predetermined locations. The dispensing may be via electrowetting.

20 Claims, 18 Drawing Sheets

Related U.S. Application Data continuation of application No. 14/262,921, filed on Apr. 28, 2014, now Pat. No. 9,061,262, which is a continuation of application No. 13/892,141, filed on May 10, 2013, now Pat. No. 9,044,724, which is a continuation of application No. 13/311,269, filed on Dec. 5, 2011, now Pat. No. 8,470,149, which is a continuation of application No. 12/709,402, filed on Feb. 19, 2010, now Pat. No. 8,163,150, which is a continuation of application No. 11/213,355, filed on Aug. 26, 2005, now abandoned.

(60) Provisional application No. 60/604,845, filed on Aug. 26, 2004.

(51) Int. Cl.
*B01L 3/02* (2006.01)
*B01L 3/00* (2006.01)
*B01J 4/00* (2006.01)

(52) U.S. Cl.
CPC ....... *B01L 3/0268* (2013.01); *B01L 3/502792* (2013.01); *B01J 2219/0036* (2013.01); *B01J 2219/00315* (2013.01); *B01J 2219/00418* (2013.01); *B01J 2219/00653* (2013.01); *B01L 2300/089* (2013.01); *B01L 2300/0816* (2013.01); *B01L 2300/0819* (2013.01); *B01L 2400/02* (2013.01); *B01L 2400/0409* (2013.01); *B01L 2400/0427* (2013.01)

(56) References Cited

U.S. PATENT DOCUMENTS

| | | | |
|---|---|---|---|
| 5,610,287 A | 3/1997 | Nikiforov et al. | |
| 5,741,462 A | 4/1998 | Nova et al. | |
| 5,980,719 A | 11/1999 | Cherukuri et al. | |
| 6,106,685 A | 8/2000 | McBride et al. | |
| 6,379,929 B1 | 4/2002 | Burns et al. | |
| 6,473,492 B2 | 10/2002 | Prins et al. | |
| 6,538,823 B2 | 3/2003 | Kroupenkine et al. | |
| 6,545,815 B2 | 4/2003 | Kroupenkine et al. | |
| 6,565,727 B1 | 5/2003 | Shenderov et al. | |
| 6,629,826 B2 | 10/2003 | Yoon et al. | |
| 6,660,480 B2 | 12/2003 | Ramsey et al. | |
| 6,665,127 B2 | 12/2003 | Bao et al. | |
| 6,761,962 B2 | 7/2004 | Bentsen | |
| 6,773,566 B2 | 8/2004 | Shenderov et al. | |
| 6,911,132 B2 | 6/2005 | Pamula et al. | |
| 6,918,309 B2 | 7/2005 | Brock et al. | |
| 6,949,176 B2 | 9/2005 | Vacca et al. | |
| 6,958,132 B2 | 10/2005 | Chiou et al. | |
| 6,989,234 B2 | 1/2006 | Kolar et al. | |
| 7,014,747 B2 | 3/2006 | Cummings et al. | |
| 7,299,749 B2 | 11/2007 | Tomita et al. | |
| 8,163,150 B2 | 4/2012 | Vann et al. | |
| 8,470,149 B2 | 6/2013 | Vann et al. | |
| 9,126,169 B2* | 9/2015 | Vann | G01N 27/44743 |
| 2001/0020588 A1 | 9/2001 | Adourian et al. | |
| 2002/0043463 A1 | 4/2002 | Shenderov et al. | |
| 2002/0058332 A1 | 5/2002 | Quake | |
| 2002/0125138 A1 | 9/2002 | Medoro | |
| 2002/0125139 A1 | 9/2002 | Chow et al. | |
| 2002/0168671 A1 | 11/2002 | Burns et al. | |
| 2002/0172969 A1 | 11/2002 | Burns et al. | |
| 2003/0006140 A1 | 1/2003 | Vacca et al. | |
| 2003/0012483 A1 | 1/2003 | Ticknor et al. | |
| 2003/0082081 A1 | 5/2003 | Fouillet et al. | |
| 2003/0103021 A1 | 6/2003 | Young et al. | |
| 2003/0164295 A1 | 9/2003 | Sterling | |
| 2003/0183525 A1 | 10/2003 | Elrod et al. | |
| 2003/0205632 A1 | 11/2003 | Kim et al. | |
| 2003/0206351 A1 | 11/2003 | Kroupenkine | |
| 2003/0224528 A1 | 12/2003 | Chiou et al. | |
| 2003/0227100 A1 | 12/2003 | Chandross et al. | |
| 2004/0007377 A1 | 1/2004 | Fouillet et al. | |
| 2004/0031688 A1 | 2/2004 | Shenderov | |
| 2004/0042721 A1 | 3/2004 | Kroupenkine et al. | |
| 2004/0055536 A1 | 3/2004 | Kolar et al. | |
| 2004/0055891 A1 | 3/2004 | Pamula et al. | |
| 2004/0058450 A1 | 3/2004 | Pamula et al. | |
| 2004/0091392 A1 | 5/2004 | McBride et al. | |
| 2004/0134854 A1 | 7/2004 | Higuchi et al. | |
| 2004/0136876 A1 | 7/2004 | Fouillet et al. | |
| 2004/0184967 A1 | 9/2004 | Parng et al. | |
| 2004/0211659 A1 | 10/2004 | Velev | |
| 2004/0231987 A1 | 11/2004 | Sterling et al. | |
| 2005/0045539 A1 | 3/2005 | Yu et al. | |
| 2005/0056569 A1 | 3/2005 | Yuan et al. | |
| 2005/0179746 A1 | 8/2005 | Roux et al. | |
| 2005/0232823 A1 | 10/2005 | Brock et al. | |
| 2006/0054503 A1 | 3/2006 | Pamula et al. | |
| 2006/0097155 A1 | 5/2006 | Adachi et al. | |
| 2006/0144706 A1 | 7/2006 | Adourian et al. | |
| 2010/0236930 A1 | 9/2010 | Vann et al. | |
| 2015/0338373 A1* | 11/2015 | Vann | G01N 27/44743 204/600 |

OTHER PUBLICATIONS

Fair, R. B. et al., "Electrowetting-Based On-Chip Sample Processing For Integrated Microfluidics", *International Electron Devices Meeting 2003, Technical Digest*, Dec. 2003, 779-782.

International Search Report for International Application No. PCT/US2005/030247 mailed Dec. 20, 2005.

International Search Report and Written opinion of the International Searching Authority for International Application No. PCT/US2005/030247 mailed Dec. 20, 2005.

Yi, et al., "Soft printing of droplets pre-metered by electrowetting,", *Sensors and Actuators A*, vol. 114, Jan. 2004, 347-354.

* cited by examiner

ELECTROWETTING DISPENSING DEVICES AND RELATED METHODS

PRIORITY

This application is a continuation of U.S. patent application Ser. No. 14/479,824 filed Sep. 8, 2014 which is a continuation of U.S. patent application Ser. No. 14/262,921 filed Apr. 28, 2014 which is a continuation of U.S. patent application Ser. No. 13/892,141 filed May 10, 2013, which is a continuation of U.S. patent application Ser. No. 13/311,269 filed Dec. 5, 2011, now U.S. Pat. No. 8,470,149, which is a continuation of U.S. patent application Ser. No. 12/709,402 filed Feb. 19, 2010, now U.S. Pat. No. 8,163,150, which is a continuation of U.S. patent application Ser. No. 11/213,355 filed Aug. 26, 2005, which claims priority to U.S. Provisional Application No. 60/604,845 filed Aug. 26, 2004, entitled "Electro-wetting Loader," which is incorporated by reference herein.

TECHNICAL FIELD

This invention relates to devices and related methods for handling and dispensing small volumes of liquids, such as, for example, in the field of microfluidics. In particular, the invention relates to devices and related methods utilizing electrowetting principles for handling and dispensing liquid for use in performing biological analysis (e.g., testing, assays, and other similar procedures).

BACKGROUND

In the field of biological analysis and assays, small amounts of liquid must often be dispensed to predetermined locations, for example, to a plurality of wells in titer plates, capillary tubes, and/or other similar test platforms, in order to perform various analyses (e.g., testing, assays, and other procedures). Such dispensing is often automated, as it is desirable to perform numerous tests at a relatively high rate. To this end, it is also desirable to dispense a large number of small volumes of liquid simultaneously. Further, it is desirable to provide precise control over the amount of liquid dispensed, the timing of the dispensing, and/or the location of the dispensing in order to prevent wasting of materials and improve efficiency of the overall testing procedure.

Conventional devices and methods for dispensing liquids, such as liquids for biological analysis, include the use of liquid handling robots and pipettes, which often are automatically controlled to dispense a predetermined amount of liquid into each well of a titer plate. Some of these liquid handling robot devices are moved to the appropriate position corresponding to a predetermined dispensing location via motors. Conventional techniques for dividing liquid into small amounts for biological analysis include the use of capillary forces, vacuum forces, and centrifugal forces, for example. Some of these conventional liquid handling devices aspirate and/or dispense liquid to some number of wells at one time. In some cases, conventional liquid handling devices can only move liquid in or out of one well at a time. This type of device typically is able to move about three axes so as to move over any well in a two-dimensional array of wells and to move toward and away from a well. Other conventional liquid handling devices may have the ability to fill multiple wells in a plate simultaneously, for example all wells in a plate, which may permit such devices to require less axes of motion to operate and to achieve faster operating rates.

Typically, such conventional dispensing devices are configured to dispense liquid to, for example, a 96 well or 384 well titer plate configuration. To achieve faster sample testing rates (e.g., a higher throughput of sample testing), it may be desirable to increase the number of testing locations (e.g, reservoirs, wells, capillary tubes, etc.) such that more samples can be dispensed onto a testing platform simultaneously and analyzed. It may further be desirable to increase the number of reservoirs (e.g., wells) on a testing platform while keeping the platforms' overall dimensions substantially the same. In other words, it may be desirable to increase the density of the testing reservoirs on the same testing platform area, such as, for example by increasing the density of the reservoirs four-fold, eight-fold, and 16-fold. In this way, new testing platforms with a larger number of testing reservoirs could be retrofit with existing analytical systems.

In some conventional liquid dispensing devices, the size of the actuators (e.g., dispensers and/or aspirators) present a practical limit to the filling density these devices are able to achieve (e.g., the number of wells the liquid dispensing devices can fill simultaneously over a titer plate having a constant area). For example, for high-density spacing between wells (e.g., relatively small distances between adjacent wells), the actuator of conventional dispensing devices may be larger than the well spacing, thereby preventing multiple actuators from addressing adjacent wells to dispense liquid simultaneously into those wells.

Thus, it may be desirable to provide devices and methods for dispensing liquid for biological analysis that provide precise manipulation of small volumes of liquid at relatively rapid rates. Further, it may be desirable to provide relatively compact dispensing devices that can provide both liquid handling (e.g., positioning) and dispensing to a plurality of locations on a testing platform. In addition, it may be desirable to provide methods and devices that can be readily incorporated into existing biological analysis systems (e.g., workstations). For example, it may be desirable to provide a dispensing device and method that can dispense liquid to a testing platform having substantially the same dimensions as conventional testing platforms while increasing the number of locations for depositing liquid for performing testing, for example increasing the number of locations (e.g., wells) to 96, 384, 768, 1536, 3072, 6144, 12,288, 24,576, etc. In other words, it may be desirable to provide dispensing devices and methods that permit higher density dispensing of liquid, including, for example, ultra-high density dispensing applications, which may improve the overall efficiency of biological analysis systems by increasing the number of tests that can be performed at a time. In providing methods and devices that permit handling and dispensing of smaller volumes of liquid at a higher density, it may further be desirable to minimize evaporation of the liquid.

Yet further desirable features include providing dispensing devices and methods that can minimize wasted liquid during dispensing, can divide an amount of supplied liquid into precise smaller amounts, and/or deliver those precise amounts accurately to predetermined locations. It also may be desirable to provide dispensing devices and methods that are capable of positioning and delivering smaller amounts of liquid than conventional dispensing devices, for example on the order of a few microliters and/or a few nanoliters.

Another desirable aspect includes providing dispensing devices and methods capable of multi-plexing, i.e., handling and dispensing multiple, differing types liquids, and capable of doing so with minimal risk of cross-contamination of the differing types of liquid.

Further, it may be desirable to provide dispensing devices that are reusable for repeated handling and dispensing operations, and to provide dispensing devices and methods that are robust, reliable, and/or reduce overall costs of handling and dispensing operations.

SUMMARY

Dispensing devices and methods according to exemplary aspects of the present invention may satisfy one or more of the above-mentioned desirable features. Other features and advantages will become apparent from the detailed description which follows.

In various applications relating to liquid handling, for example in the field of microfluidics, electrowetting has been used to manipulate liquid behavior. As used herein, electrowetting involves the use of an electric field to alter the wetting behavior of liquid relative to a surface so as to control the movement of the liquid. In other words, through the application of an electric potential, a liquid-solid interface can be altered by controlling the wettability of the surface (e.g., effectively converting the surface in contact with the liquid from hydrophobic to hydrophilic or vice versa) to thereby control movement of a liquid on that surface. Thus, electrowetting can be used to precisely divide and position liquid, without the need to utilize pumps, valves, channels, and/or other similar fluid handling mechanisms.

As an example, electrowetting may include sandwiching the liquid between two plates and in contact with an insulated electrode. By applying an electric field in a non-uniform manner so as to create a surface energy gradient, a large number of small volumes of liquid (e.g., droplets, beads, cells, or other small volumes) can be independently manipulated under direct electrical control and without the use of pumps, valves, or fixed channels. Moreover, as will be explained in the description which follows, electrowetting may be used to achieve relatively precise movement of liquid on a surface in relatively larger amounts, e.g., without necessarily requiring first dividing the liquid into droplets or the like.

For further information on electrowetting and exemplary device configuration and applications for implementing electrowetting, reference is made to U.S. Pat. No. 6,565,727 B1, which issued on May 20, 2003; U.S. Publication No. 2003/0205632 A1, which published on Nov. 6, 2003, and U.S. Publication No. 2003/0006140 A1, which published on Jan. 9, 2003, the entire contents of each of which are incorporated by reference herein. To the extent that any conflict may exist between the teachings of the above-cited patent documents and this application, the teachings of this application should apply.

In accordance with exemplary aspects of the invention, the use of electrowetting in the field of liquid handling for biological analysis may provide relatively accurate and fast manipulation of a large number of small volumes of liquid. As discussed above, there is a need for dispensing liquid used in biological analysis (e.g., assays, testing, and other related procedures) into numerous small reservoirs, such as wells in titer plates, for example, with a compact device (e.g., loader) that provides both liquid handling (e.g., positioning) and dispensing. Such a device may replace a liquid handling robot or be incorporated within a biological analysis workstation. The loading configuration of the dispensed liquid may be programmed by computer, e.g. a 96-, 384-, 768-, 1536-, 3072-, 6144-, 12,288-, or 24,576-well format. The amount of liquid dispensed may include drops, cells, beads, or other amounts, in an exact number (e.g., the amount of liquid dispensed may be controlled). Moreover, the precise locations to which the liquid is dispensed may be controlled.

According to exemplary aspects of the invention, supplied liquid may be divided into smaller, precise portions (e.g., volumes) and dispensed. The dispensed volumes can be very small, for example, on the order of a few microliters and/or a few nanoliters. By way of example only, the dispensed volumes may range from about 0.01 microliters to about 100 microliters, for example from about 0.01 microliters to about 5 microliters. In an exemplary aspect, the volume may be about 1 microliter. A wide range of volumes are envisioned depending on the particular application. Further, according to another exemplary aspect, a dispensing device may handle multiple, differing types of liquid samples (e.g., multi-plexing). For example, a dispensing device according to aspects of the invention may have more than one sample input port such that differing samples can be input to the device via differing input ports, moved and positioned in a segregated fashion throughout the dispensing device, and then distributed to differing locations of a testing platform. In an alternative example, differing liquids may be input via differing ports and mixed together within the dispensing device and then dispensed to the testing platform. Since the dispensing devices and methods according to aspects of the invention may be programmable, the chance of cross-contamination when performing multi-plexing procedures may be reduced.

A dispensing device (e.g., loader) according to exemplary aspects of the invention may replace sample-positioning motors by manipulating drops into view. For example, if an operator is looking through a microscope at a marked electrode in a transparent dispensing device, the operator can manipulate a sample drop into the microscope view without having to first find the location of the sample in the dispensing device prior to looking through the microscope.

Assuming the input and dispensed volumes of liquid are the same, dispensing devices and methods according to aspects of the present invention may minimize wasted liquid as compared to conventional fluid dispensing devices. Further, according to yet another exemplary aspect, evaporation of liquid may be minimized when dividing liquid into relatively small volumes and dispensing those small volumes to relatively high density testing platform formats.

According to yet an additional exemplary aspect, when dispensing liquid to capillaries, reagent costs may be reduced, for example by orders of magnitude. At least some of the dispensing devices and methods according to aspects of the invention result in a robust and reliable handling and dispensing operation. Moreover, in an exemplary aspect, the dispensing devices may be reusable for repeated dispensing of samples.

According to an exemplary aspect of the invention, as embodied and broadly described herein, the invention may include a method for dispensing liquid for use in biological analysis comprising positioning liquid to be dispensed via electrowetting. The positioning may comprise aligning the liquid with a plurality of predetermined locations. The method may further comprise dispensing the aligned liquid from the plurality of predetermined locations through a plurality of openings respectively aligned with the predetermined locations.

According to yet another exemplary aspect, the invention may include a method for dispensing liquid for use in biological analysis comprising supplying a liquid to be dispensed to a housing comprising an interior surface and altering a wettability of the interior surface so as to divide the liquid in the housing into a plurality of individual portions of liquid and to move the plurality of individual portions of liquid to a plurality of respective predetermined locations. The method may further comprise dispensing the plurality of individual portions of liquid from the plurality of predetermined locations through a plurality of openings respectively aligned with the plurality of predetermined locations.

In the following description, certain aspects and embodiments will become evident. It should be understood that the invention, in its broadest sense, could be practiced without having one or more features of these aspects and embodiments. It should be understood that these aspects and embodiments are merely exemplary and explanatory and are not restrictive of the invention.

BRIEF DESCRIPTION OF DRAWINGS

The accompanying drawings, which are incorporated in and constitute a part of this specification, illustrate embodiments of the invention and together with the description, serve to explain certain principles. In the drawings.

DETAILED DESCRIPTION

Figure 1:
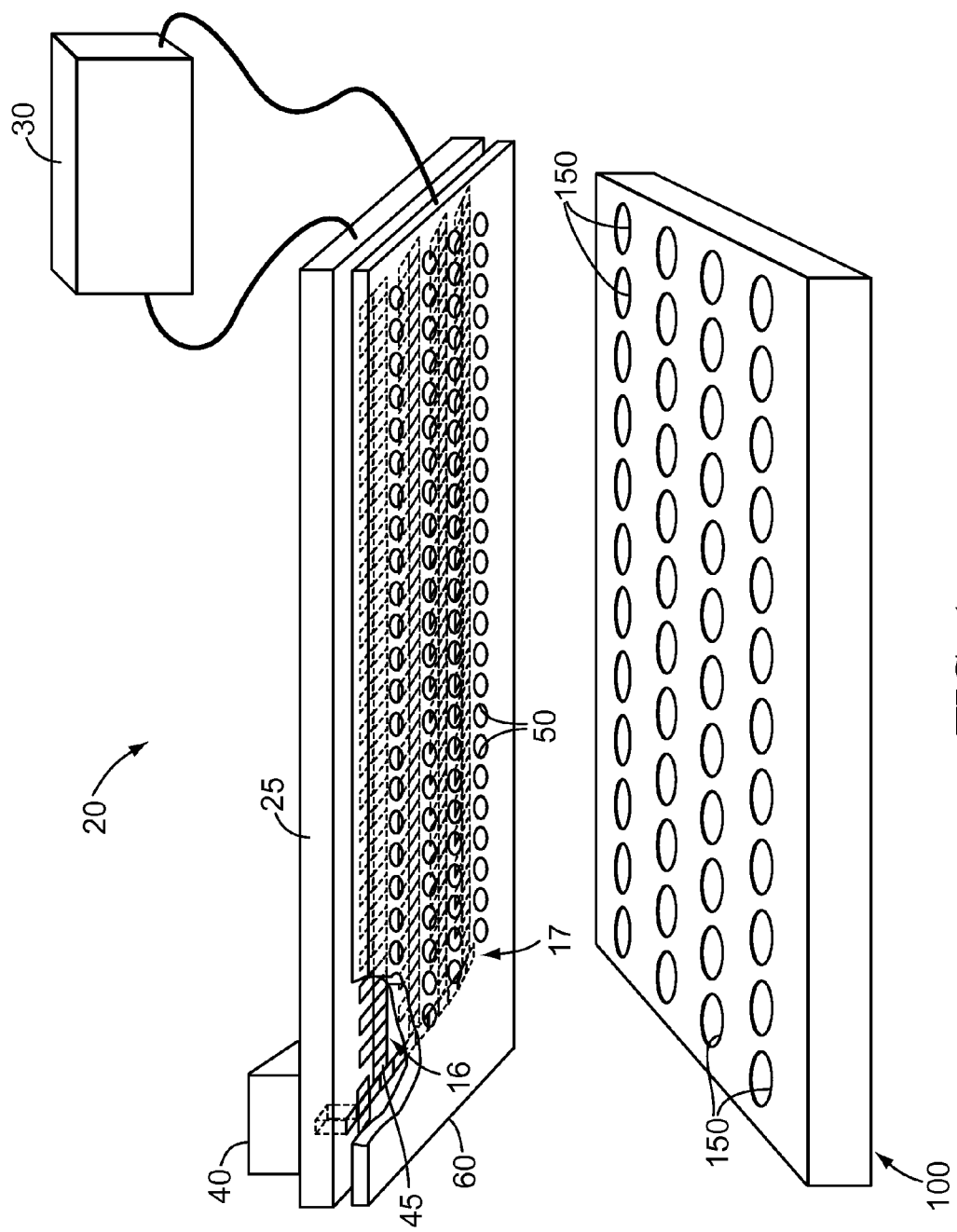
FIG. 1 is a schematic, perspective view of an exemplary embodiment of a dispensing device configured for dispensing liquid to a titer plate according to an aspect of the invention.

FIG. 1 shows an exemplary embodiment of a dispensing device according to aspect of the invention. The dispensing device 20 shown in FIG. 1 is referred to herein as an electrowetting loader (EWL). In the exemplary embodiment of FIG. 1, the EWL 20 is shown in conjunction with a titer plate 100 comprising a plurality of wells 150 to which the EWL 20 is configured to dispense small portions (e.g., volumes) of liquid for biological analysis. The EWL 20 comprises a first substrate 25. A plurality of electrodes 45, which may be in the form of electrical pads, for example, are embedded in the first substrate 25. As shown in FIG. 1, the electrical pads 45 may be arranged so as to form a two-dimensional array of rows 16 and columns 17. Each pad 45 in the substrate 25 can be independently charged positive or negative relative to a power source provided in an electrical controller 30. For example, each pad 45 may be separately wired to the controller 30.

A thin, hydrophobic insulator layer 24 may cover the electrical pads 45, as shown in FIGS. 2A-2D. An input port 40, which may be in the form of a hydrophilic through-hole, for example, in the substrate 25 permits loading of a first amount of liquid, for example, several milliliters, into the EWL 20. By way of example, to fill a 1536-well format titer plate with 4 microliters per well, at least 6.144 milliliters of liquid may be supplied from the input port 40 to the dispensing device 20. As will be explained in more detail below, the electrical pads 45 may be arranged in columns 17 and rows 16 so as to separate, position, and dispense a plurality of individual exact (e.g., predetermined) volumes of liquid supplied from the input port 40 and move those individual volumes, which may be in the form of droplets, for example, in any two dimensional movement within the EWL 20 that is desired.

The EWL 20 further comprises a second substrate 60 disposed substantially opposite the first substrate 25 and separated from the first substrate 25 by a small distance (for example, ranging from about 0.1 millimeters to about 10 millimeters, such as, for example, about 1 millimeter.) A seal 65, such as, for example, adhesive (e.g., double-sided tape), a polymer gasket, metallic seals, or other similar seals, may be provided along the edges of the substrates 25, 60, as shown in FIGS. 2A-2D, to hold the substrates 25, 60 spaced apart from one another. The seal 65 may define, in conjunction with the substrates 25, 60, a chamber 70 (e.g., cavity) configured to receive liquid from the input port 40 and to move and position the liquid inside the EWL 20. The second substrate 60 may have one relatively large embedded electrode 75 that can be independently charged positive or negative relative to the power source associated with the electrical controller 30. That is, the electrode 75, like the electrodes 45, may also be separately wired to the controller 30. As shown in FIGS. 2A-2D, a thin, hydrophobic insulator layer 74, which may be similar to insulator layer 24, may cover the electrode 75.

Thus, the first substrate 25, second substrate 60, and seal 65 together may form a housing having an interior surface, which in the exemplary embodiment of FIGS. 1 and 2, includes the surfaces of insulator layers 24, 74 facing chamber 70. At least one interior surface portion of the housing may be configured so as to be electrically conductive. For example, at least one interior surface portion may comprise a dielectric material covering an electrical conductor, such as, for example, the insulator layers 24, 74 covering the electrodes 45, 75 in the embodiment of FIGS. 1 and 2.

The second substrate 60 may define at least one opening therethrough, e.g., a plurality of openings 50. The openings 50 may be in the form of small, hydrophilic through-holes (e.g., exit ports) that can be arranged and configured so as to align with predetermined locations (e.g., reservoirs) on a testing platform. For example, as shown in FIG. 1, the openings 50 may be configured and arranged so as to align with wells 150 in a titer plate 100. That is, the number and arrangement of the openings 50 may have substantially the same number and arrangement of a particular titer plate format, e.g., 96-, 384-, 768-, 1536-, 3072-, 6144-, 12,288-, or 24,576-well format.

According to an exemplary aspect, the openings 50 may be lined with (e.g., coated with a layer of) a material that exhibits hydrophilic characteristics. In an alternative embodiment, the openings 50 may be configured so as to be capable of exhibiting hydrophilic characteristics upon application of an electric field thereto. In other words, in a manner similar to that which will be described below with reference to the nozzle plate of FIGS. 9, 10 and 13, the openings 50 may be configured so as to be capable of drawing liquid to be dispensed into the openings 50 via electrowetting. In either case, during filling, the openings 50 may exhibit hydrophilic characteristics such that the liquid moves from predetermined locations within the chamber 70 into the openings 50. In the example wherein the openings are configured to become hydrophilic, prior to filling the openings with liquid, the openings may exhibit hydrophobic characteristics.

FIGS. 2A-2D schematically illustrate a side, cross-sectional view of the EWL of FIG. 1 and illustrate how the EWL 20 aliquots a portion (e.g., first amount) of the liquid supplied to the housing (e.g., chamber 70) from the input port 40 into small portions (e.g., droplets) of predetermined volume less than the first amount and moves those droplets through the chamber 70 via electrowetting so as to ultimately be dispensed through one or more openings 50. For ease of reference, only a portion of the EWL 20 is illustrated to show how the electric charge of the electrodes 45, 75 can be controlled (e.g., via controller 30) so as to move liquid within the chamber in a single direction to be positioned in alignment with an opening 50 for dispensing therethrough. FIG. 3, discussed below, schematically illustrates how liquid can be moved in two dimensions within the chamber 70 and aligned with predetermined locations by arranging the electrical pads 45 in a two-dimensional array of rows and columns and controlling the charge of the pads 45 in a manner similar to that described with reference to FIG. 2.

Figure 2A:
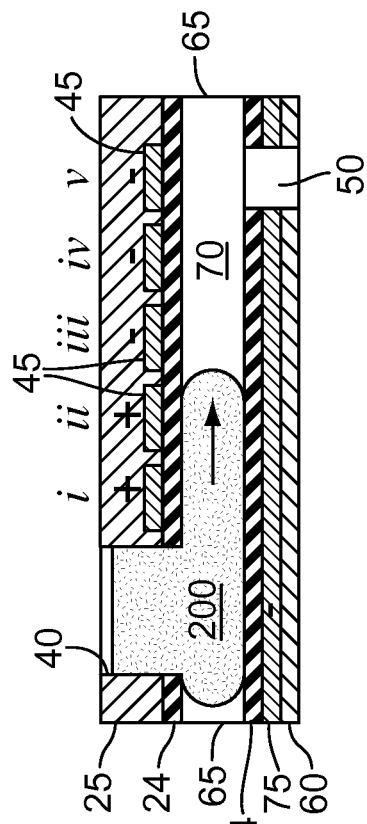
FIGS. 2A-2D illustrate a schematic, partial cross-section of the dispensing device of FIG. 1 and various exemplary steps for positioning and dispensing a liquid according to aspects of the invention.

Referring to FIG. 2A, a relatively large volume of liquid 200 (on the order of several milliliters) is supplied to the input port 40. By way of example, the input volume of liquid may range from about 0.1 microliter to about 10 milliliters. The liquid fills the hydrophilic port 40 but is prevented from moving (e.g., spreading) into the chamber 70 of the EWL 20 by the hydrophobic insulator 24 provided on the surface of the substrate 25 facing the chamber 70. In other words, because the input port 40 extends into the chamber, liquid is able to fill the hydrophilic port 40 so as to touch the insulator layer 74 of the second substrate 60. However, portions of the hydrophobic surfaces 24, 74 adjacent the input port 40 act to repel the liquid 200, thereby preventing the liquid 200 from moving away from the input port 40 and further into the chamber 70.

Figure 2B:
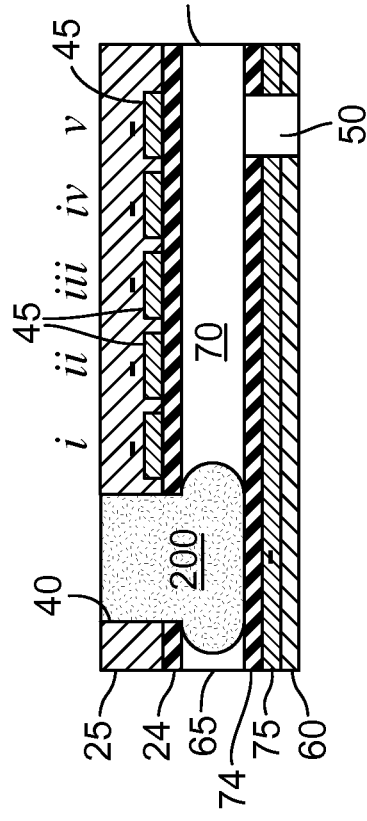

As shown in FIG. 2B, once it is desired to begin moving the liquid from the input port 40 throughout the chamber 70, power may be supplied from the controller 30 so that the electrode 75 of the second substrate 60 may be negatively charged while the first two electrical pads 45 adjacent to the input port 40 (e.g., the pads occupying positions i and ii labeled in FIG. 2) are positively charged. The relative charges of the electrodes are indicated by +/− in FIGS. 2A-2D. By altering the electric potential in this manner, a charge builds up at the insulator surface 24 but not on the insulator surface 74 of the second substrate 60. Supplying the pads 45 with a positive electrical charge, relative to the negative electrical charge of the electrode 75, effectively converts the pads 45 into electrical capacitors and causes the wetting angle at the surface portion of the insulator 24 facing the chamber 70 and positioned below the positively charged pads 45 (e.g., the insulator 24/liquid 200 interface) to change from hydrophobic to hydrophilic. In other words, by controlling the electric charge, the wettability of the surface portion in contact with the liquid is altered so as to control movement of the liquid. The now converted hydrophilic surface corresponding to the location of those positively charged pads, e.g., at position i and ii in FIG. 2B, draws liquid 200 from the port 40. The liquid 200, however, does not travel further to the pad 45 occupying position iii because that pad 45 is negatively charged in FIG. 2B.

Figure 2C:
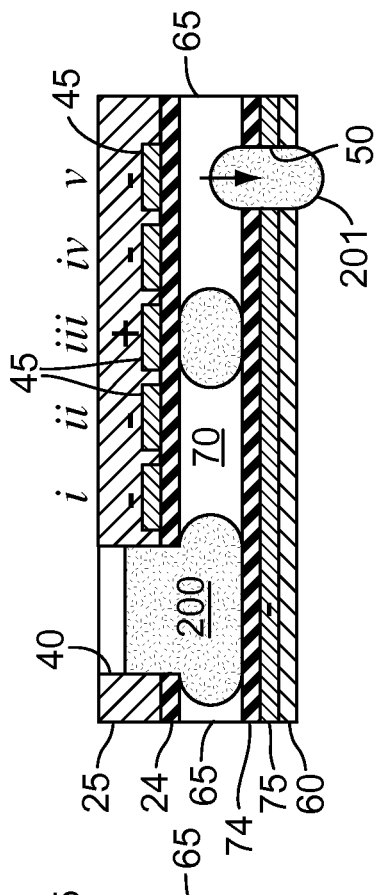

FIG. 2C demonstrates an example of how liquid can be drawn further into the chamber 70 and cut into an individual portion (e.g., an independent droplet) of liquid. As shown and explained above with reference to FIG. 2B, the first and second pads 45 adjacent to the port 40 (e.g., pads 45 occupying positions i and ii, respectively) are positively charged such that liquid wets the surface below them. To divide the liquid 200 in the chamber 70 into a smaller portion, such as, for example, droplet 201, the pad 45 occupying position ii is positively charged and pad 45 occupying position i as well as pads 45 on both sides of the pad 45 occupying position i (perpendicular to the plane of FIG. 2C and not shown) are negatively charged. Controlling the electric charges in this manner creates a force that squeezes a portion of the liquid 200 into an independent droplet 201 resting on the surface corresponding to the positively charged pad 45 occupying position ii. In other words, as explained above, the negatively charged pads essentially return the portion of the surface of the insulator 24 facing the chamber 70 and positioned in alignment with those negatively charged pads to the original hydrophobic state, altering the wettability of the surface portion (e.g., the liquid/surface contact angle) from its previous state and thereby repelling the liquid away from it and toward the surface portion of the insulator 24 positioned in alignment with the positively charged pad 45 occupying position ii.

Once a droplet 201 of the liquid is cut, further controlling the charge of pads 45 at positions surrounding the droplet can move a drop along columns and rows substantially from pad to pad. In an exemplary aspect, the droplet volume may be designed to slightly overflow onto all pads that occupy positions adjacent to the pad at which a droplet is located. To move the individual droplet from one pad (the resting pad) to another adjacent pad, the adjacent pad to which it is desired to move the droplet is made positively charged such that the insulator surface portion at a location corresponding to that pad becomes hydrophilic and attracts the droplet. At the same time, the resting pad is made negatively charged such that the insulator surface portion at the location corresponding to that pad becomes hydrophobic, repelling the droplet to thereby push the droplet off the resting pad and onto the adjacent pad. This procedure of controlling the charge of the electrical pads 45 can move a droplet indefinitely along a row of pads, including turning corners so as to permit the droplet to travel along a column of pads.

Figure 2D:
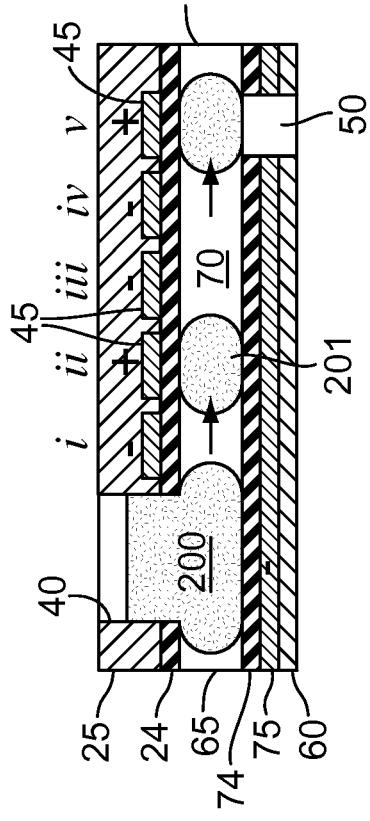

FIG. 2D illustrates an example of how a droplet 201 may be drawn into an opening 50 (e.g., throughhole) in the second substrate 60. Hydrophilic openings 50 in the second substrate 60 may be disposed such that they are substantially opposite to at least some of the electrical pads 45 in the first substrate 25. By controlling the charges of the electrical pads 45, including an electrical pad 45 aligned with the opening 50 (e.g., the pad occupying position v in FIG. 2D), a droplet 201 can be attracted to the pad 45 when the pad 45 is positively charged and subsequently drawn into the opening 50 by capillary force so as to fill the opening 50. If the outer surface (the surface facing away from chamber 70) of the second substrate 60 is hydrophobic, and the opening 50 is appropriately sized and configured, the droplet 201 will not flow out of the opening 50 absent some additional force acting on the droplet 201 to express it from the opening 50. Various exemplary devices and methods for dispensing droplets from the openings 50 will be explained below with reference to FIGS. 4-7.

FIG. 3 shows an exemplary embodiment of how multiple droplets 201 can be cut and moved through the EWL chamber 70 in two dimensions such that the multiple droplets 201 can fill respective multiple openings 50 in a chosen format. As with FIG. 2, only a small portion of the electrical pad arrangement embedded in the first substrate 25 is illustrated for ease of reference. It should be understood that the number of electrodes and arrangement thereof can vary depending on such factors as the desired movement of the individual portions of liquid, the volume of the individual portions of liquid to be dispensed, the desired positioning of the individual portions of liquid prior to dispensing, the arrangement and configuration of the openings in the second substrate, the testing platform format, and/or other factors relating to the desired application in which the dispensing device will be utilized.

In various other embodiments, and in accordance with aspects of the invention, the electrodes may be replaced with photosensitive material permitting control over the liquid (e.g., including over droplets) by incident light as described in U.S. Application Publication No. 2003/0224528 A1, which published on Dec. 4, 2003, the entire content of which is incorporated by reference herein. To the extent that any conflict may exist between the teachings of the above-cited published application and this application, the teachings of this application should apply.

Figure 3A:
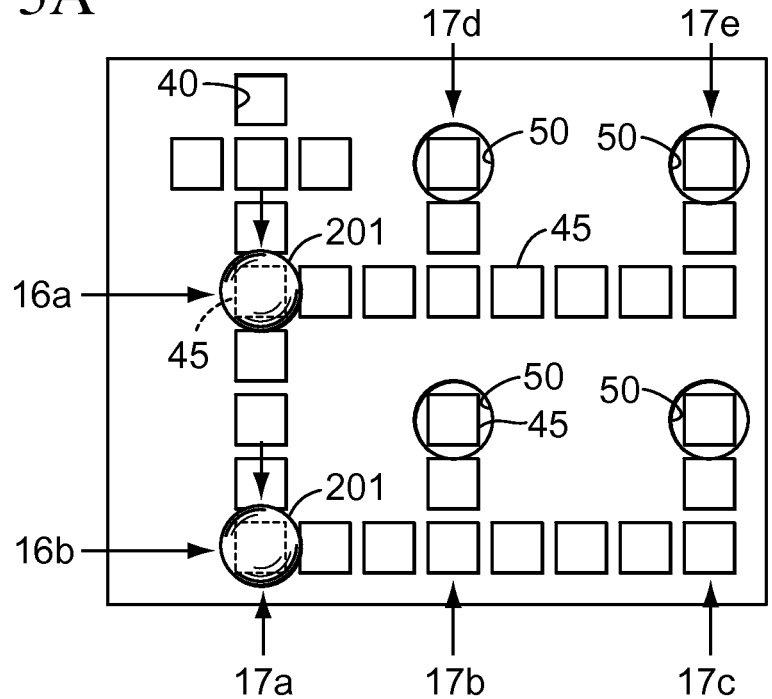
FIGS. 3A-3D schematically illustrate exemplary steps for positioning liquid in a dispensing device according to aspects of the invention.

With reference to FIG. 3A, droplets of liquid 201 are first cut from the input port 40 as described with reference to FIG. 2B above. For the example shown in FIG. 3, four droplets 201 of liquid will be cut and eventually moved throughout the chamber of the EWL 20 to four respective openings 50 in the second substrate. The droplets 201 are first moved along a first column 17a of electrodes (e.g., electrical pads 45) that aligns with the input port 40. The movement of the droplets 201 along the electrical pads 45 in the column 17a can be achieved by controlling the relative electrical charges of the pads 45, as described with reference to FIG. 2C above. As shown in FIG. 3A, the droplets 201 are brought to respective positions along the column of electrical pads at which rows 16a, 16b of electrical pads 45 intersect the column 17a.

Figure 3B:
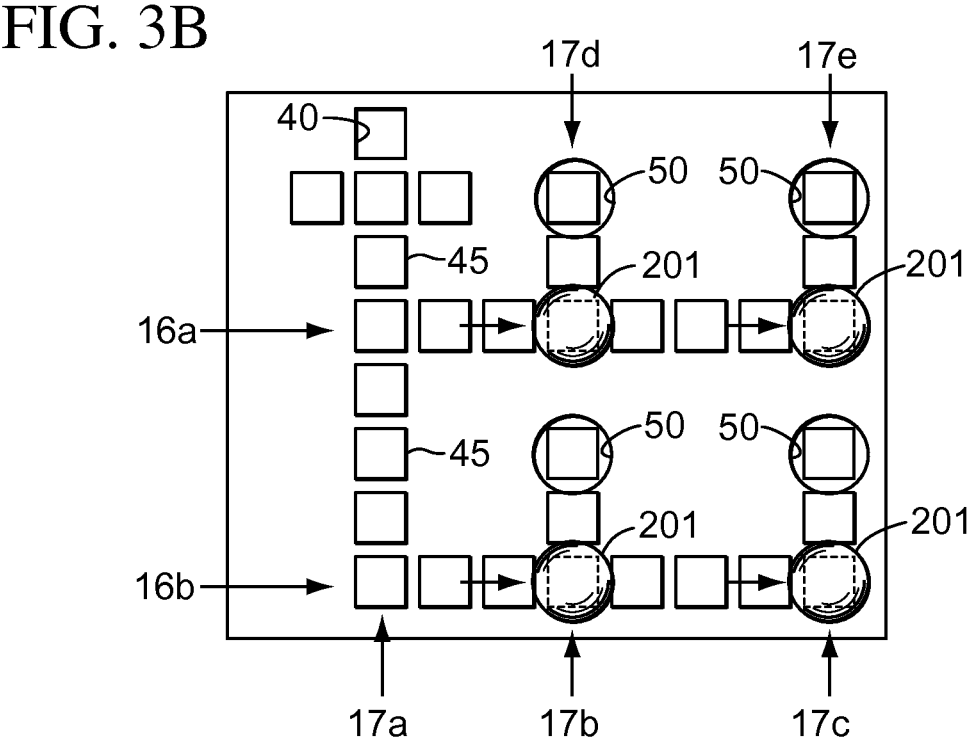

In FIG. 3B, the droplets 201 are directed at a right angle onto the intersecting electrode rows 16a, 16b. The droplets 201 are moved along the rows 16a, 16b and positioned again at row-column intersections. That is, the droplets 201 are moved respectively to electrical pads 45 in rows 16a, 16b that intersect with additional (e.g., secondary) columns 17b, 17c, 17d, 17e of electrical pads 45. Each of these columns 17b, 17c, 17d, 17e ends with an electrical pad 45 being positioned substantially in alignment with openings 50 in the second substrate 60.

Figure 3C:
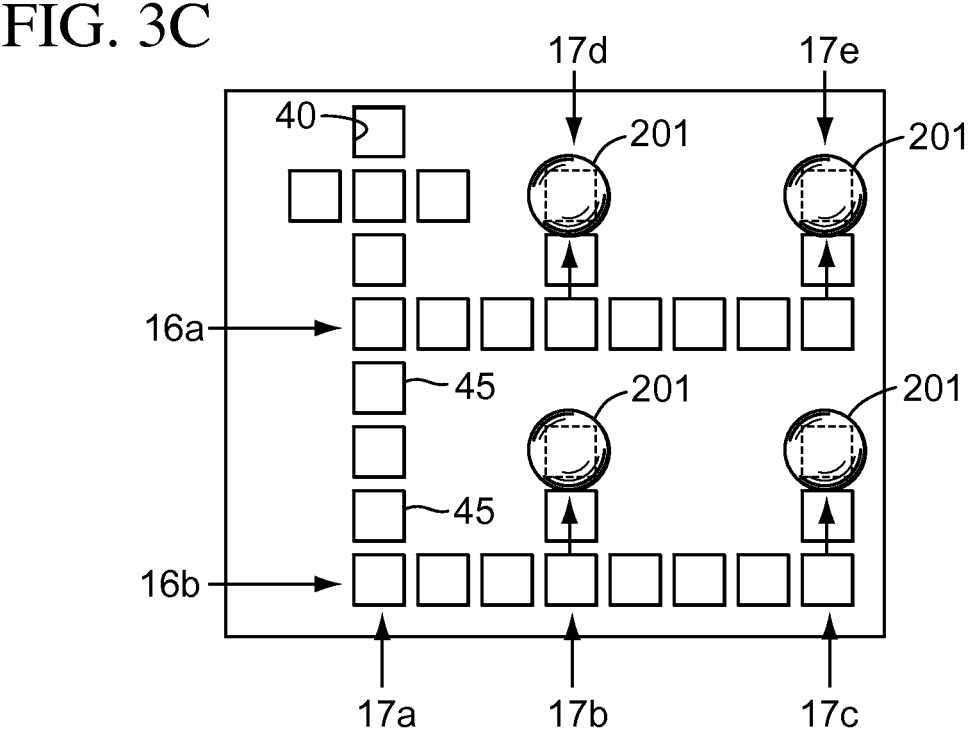
Figure 3D:
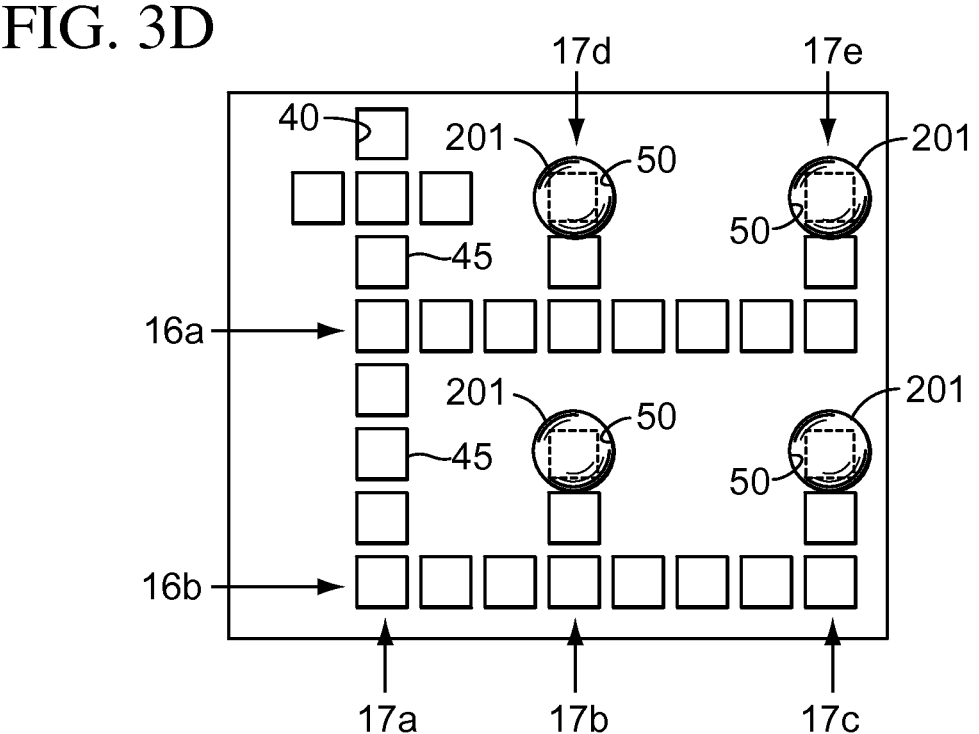

FIG. 3C illustrates an example of how the droplets 201 may be moved along secondary columns 17b, 17c, 17d, 17e into positions (e.g., to predetermined locations) that are respectively aligned with the holes 50. FIG. 3D illustrates how the droplets 201, once positioned appropriately, may be drawn into the holes 50, such as, for example, by capillary force as explained with reference to FIG. 2 above.

Once positioned within the EWL 20 and drawn into the holes 50, the individual droplets 201 are ready to be dispensed from the EWL 20 to a plurality of predetermined locations on a testing platform, such as wells in a titer plate, capillary tubes, or locations on a microscope slide, for example. FIGS. 4-7 illustrate exemplary embodiments for various techniques to achieve the dispensing of the droplets 201 from holes 50 to a testing platform so that biological analysis procedures can be performed.

Figure 4A:
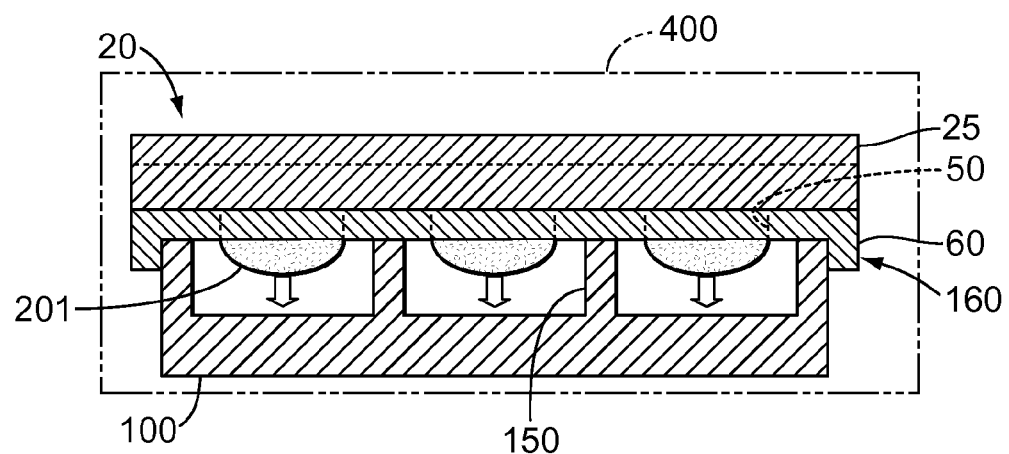
FIGS. 4A and 4B are schematic partial views of an exemplary embodiment for dispensing liquid from the dispensing device of FIG. 1 into wells in a titer plate.

FIG. 4 shows an exemplary embodiment of a technique for dispensing the droplets 201 from the EWL 20 to a plurality of wells 150 in a titer plate 100 using centrifuging. In the schematic illustration of FIG. 4A, a partial, side cross-sectional view of the EWL 20 is shown with droplets 201 drawn into the holes 50 and held therein via capillarity. In the exemplary embodiment of FIG. 4A, the second substrate 60 of the EWL 20 is clamped into contact with the well-side of the titer plate 100 via a clamping mechanism 160. Suitable clamping mechanisms for clamping the EWL 20 and titer plate 100 together may include, but are not limited to, the use of snap fit mechanisms, elastic bands, springs, gravity, screws, bolts, and/or mechanical pressure, for example. The clamping may occur prior to the start of the loading/positioning of the liquid within the EWL 20. The centers of the EWL holes 50 may be substantially aligned with the centers of the wells 150. After electrowetting is utilized to fill the holes 50 with liquid droplets 201, for example, as described above with reference to FIGS. 2 and 3, the titer plate 100 and EWL 20 are placed in a centrifuge 400 and centrifuged together such that the droplets 201 are forced from the holes 50 and into the respectively aligned wells 150.

Figure 4B:
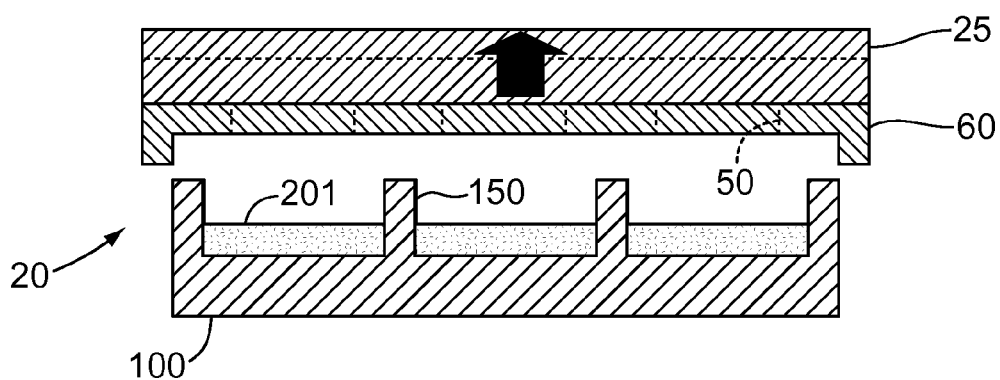

Once the droplets 201 are dispensed to the wells 150, the EWL 20 may be unclamped and removed from contact with the titer plate 100, as shown in FIG. 4B. The titer plate 100 may then be brought to a station or the like to perform biological analysis on the liquid 201 in the wells 150.

Though FIG. 4 illustrates an exemplary embodiment of dispensing droplets 201 from the EWL 20 into wells of a titer plate, it should be understood that a similar method could be used to dispense droplets via centrifuge onto predetermined locations of a two-dimensional surface such as, for example, a microscope slide.

Figure 5A:
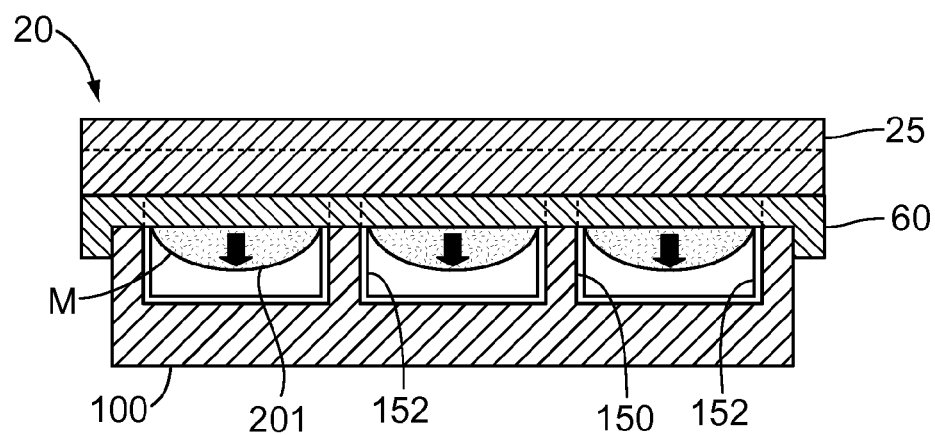
FIGS. 5A and 5B are schematic partial views of another exemplary embodiment for dispensing liquid from the dispensing device of FIG. 1 into wells in a titer plate.
Figure 5B:
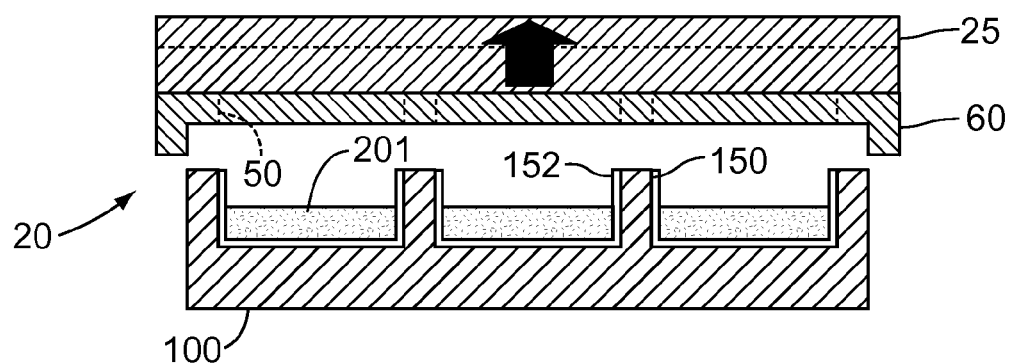

FIG. 5 schematically illustrates another exemplary technique for dispensing droplets 201 from the EWL 20. The exemplary embodiment of FIG. 5 demonstrates a technique whereby wells 150 in a titer plate 100 are coated with a hydrophilic material 152 and used to draw the droplets 201 into the wells 150 from the holes 50 in the EWL 20. As in FIG. 4A, the second substrate 60 of the EWL 20 may be clamped into contact with the well-side of a titer plate 100 prior to the start of loading and positioning of the liquid in the EWL 20. The centers of the EWL holes 50 may be substantially aligned with the centers of the wells 150. Electrowetting may then be utilized to fill the holes 50 with the droplets 201 of liquid.

In the exemplary technique of FIG. 5, the volume of each droplet 201 may be selected so as to be greater than the volume of the hole 50 through which the droplet 201 is dispensed such that the droplet 201 extends out of the hole 50 and forms a meniscus M, as shown in FIG. 5A, when it is held in the hole 50 via capillarity. The hole 50 may be designed such that its diameter is slightly larger than the diameter of the corresponding well 150 to which it is aligned. This configuration permits the meniscus M to touch the lateral wall of the well 150 when the droplet 201 passes through the hole 50. The hydrophilic coating 152 provided on the inside surface of the well 150 may then attract the droplet 201, drawing the droplet 201 from the hole 50 into the well 150. According to an exemplary aspect, only the inside of the well wall is made hydrophilic such that the droplet is attracted into the well rather than on the top of the plate, which may be hydrophobic.

Examples of suitable hydrophilic materials that could be used to coat the inside of the wells 150 include cations, anions, polyethylene oxides, sugars, polyacrylamides, surfactants, and other hydrophilic materials. By way of example, amphiphilic, di-block copolymers may be used to coat the inside of the wells 150. Aside from coating the wells with a hydrophilic material, it should be understood that any technique may be utilized to provide the wells with a hydrophilic inner surface, such as for example, bonding a layer of such material to the well inner surface, forming the wells out of a hydrophilic material, and other techniques.

Yet a further exemplary technique for dispensing the droplets from the EWL 20 to a testing platform includes the use of electrowetting. In the exemplary embodiment of FIG. 6, electrowetting is utilized to cause the droplets 201 to be dispensed from their positions within respective holes 50 to a testing platform. Using electrowetting to move the droplets from the EWL 20 to a testing platform may obviate the need for centrifugal dispensing, which may cause relatively violent motions on a micro-scale and potentially result in cross-contamination between wells. Further, centrifugation may require additional hardware, e.g., a centrifuge, and additional steps, which may make automation more difficult.

Figure 6A:
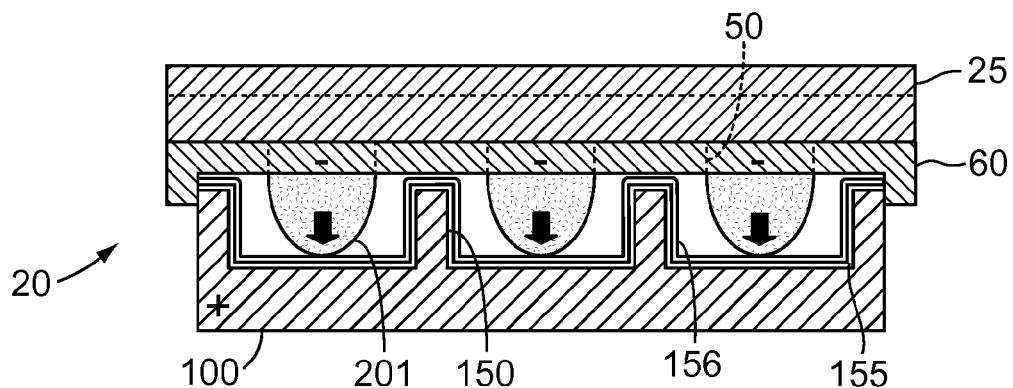
FIGS. 6A and 6B are schematic partial views of yet another exemplary embodiment for dispensing liquid from the dispensing device of FIG. 1 into wells in a titer plate.
Figure 6B:
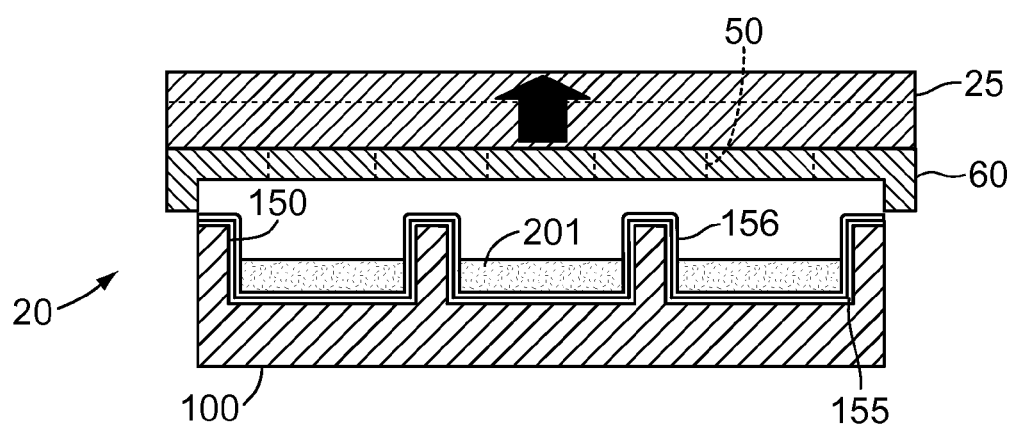

In the exemplary embodiment of FIG. 6, a titer plate 100 (e.g., a microtiter plate) is substantially uniformly coated with a thin layer of an electrically conductive material 155, for example an electrically conductive metal, such as, for example, gold, aluminum, indium tin oxide, or other electrically conductive material. By way of example, the thickness of the metal layer may range from about 50 angstroms to a few micrometers. For example, the thickness may be about 500 nanometers. The metal layer 155 may be deposited via a variety of known techniques, including but not limited to vapor deposition, spray coating, electroplating, chemical vapor deposition, sputtering, spin coating, emersion, and other deposition techniques, for example. The deposited layer 155 may then be electrically isolated by providing a hydrophobic layer 156 over the layer 155. The hydrophobic layer 156 may be made from a polymeric material, such as, for example, cyclic olefin polymer, polymethyl methacrylate (PMMA), or Teflon-AF™, and may be applied by any suitable technique, such as, for example, spray coating, spin coating, dip coating, in situ polymerization, and/or other coating techniques. The thickness of the hydrophobic layer may range from about 0.1 micrometers to several micrometers, and may be, for example, about 0.1 micrometers. According to an exemplary aspect, the testing platform (e.g., titer plate, card, etc.) may be made of a hydrophobic material such that masking it from a hydrophilic coating may suffice for a hydrophobic barrier. According to some aspects, the hydrophobic layer may have a thickness on the order of approximately 500 nm.

As with the exemplary techniques of FIGS. 4 and 5, the EWL 20 may be clamped via a clamping mechanism 160 to the well side of a titer plate 100, as shown in FIG. 6A, prior to loading and positioning the droplets 201 within the EWL 20. The centers of the EWL holes 50 may be substantially aligned with the centers of the wells 150. Electrowetting may then be utilized to fill the holes 50 with the droplets 201 of liquid, as described above.

When it is desired to dispense the droplets 201 from the holes 50 to the wells 150, movement of the droplets 201 may be actuated by applying a negative potential to both the first and second EWL substrates 25, 60 (shown in FIGS. 2D and 6A) and applying a positive potential to the metal layer 155 deposited on the titer plate 100. This renders the EWL substrates 25, 60 hydrophobic and the titer plate layer 156 hydrophilic, resulting in the droplets 201 being attracted to the titer plate 100 and being drawn into the wells 150 by capillary wicking when the droplets 201 touch the wells 150. Thus, in the exemplary embodiment of FIG. 6, electrowetting is used to dispense the liquid droplets 201 from the EWL 20.

Numerous procedures exist in micromachining literature for coating polymer substrates, such as a titer plate, with metals. It is envisioned that any of these methods may be used to coat the titer plate (or other testing platform) with a metal layer as desired. One exemplary method of forming a metal layer on such a substrate is by using physical vapor deposition (PVD). Typically, the polymer substrate is activated by treatment with oxygen plasma (corona discharge), which may be followed by PVD of, for example, chromium, tungsten, or titanium adhesion layers, which in turn may be followed by PVD of, for example, gold. All of these operations may be performed under high vacuum environments to prevent oxidation of adhesion layers. Alternate methods for depositing metal layers on a substrate, such as a polymer substrate, for example a titer plate, include metal deposition by sputtering, electro-deposition, electro-chemical-deposition, electro-less deposition, and other deposition techniques. As discussed above, the hydrophobic layer can be applied to the metal surface by spin coating, dip coating, in situ polymerization, spray coating, and/or other coating techniques.

Figure 7:
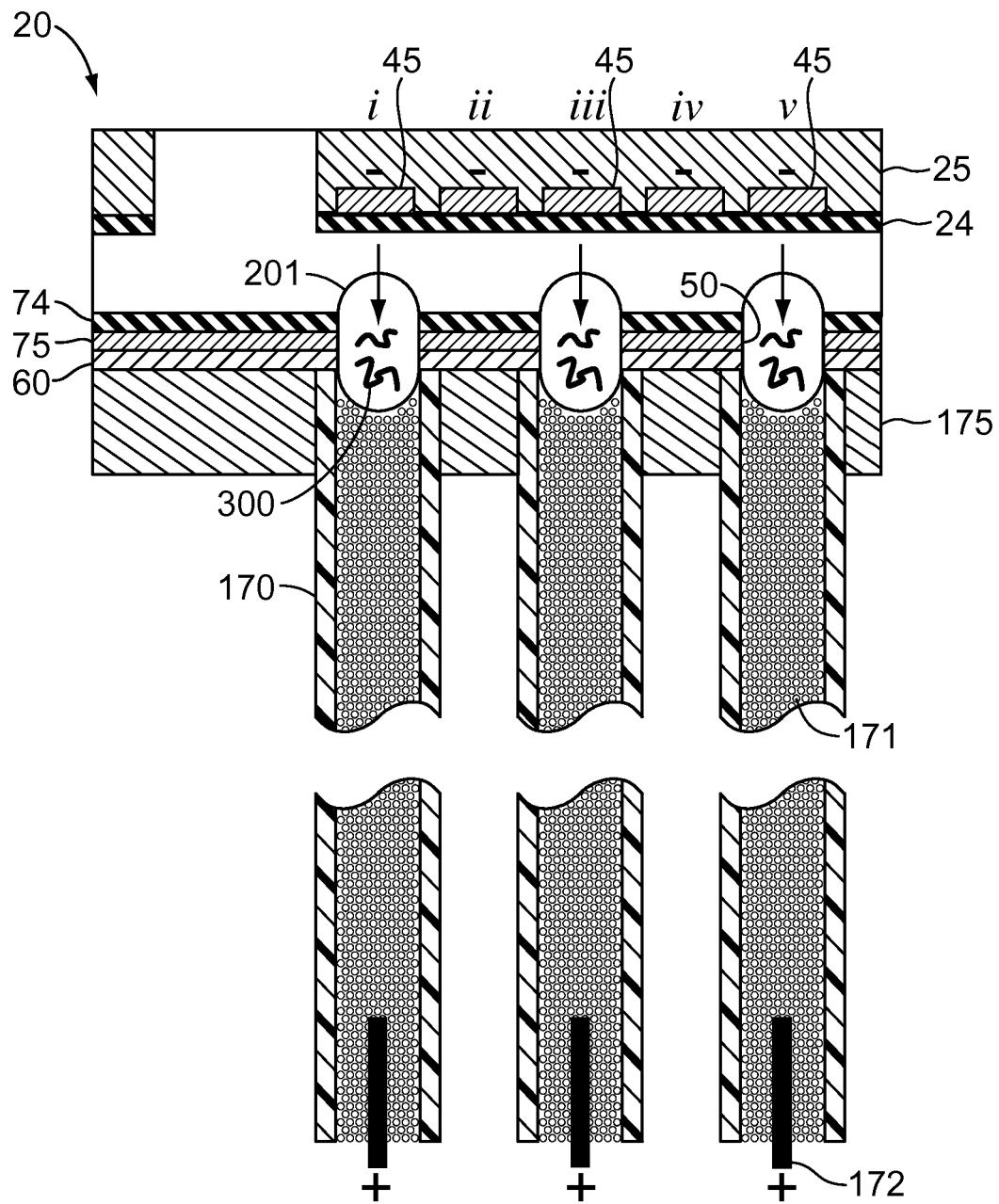
FIG. 7 is a schematic partial view of an exemplary embodiment for dispensing liquid from the dispensing device of FIG. 1 to capillary tubes.

Yet a further exemplary technique for dispensing the droplets 201 from the EWL 20 after they have been positioned as desired and moved into the holes 50 of the second substrate 60 is illustrated in FIG. 7. FIG. 7 illustrates a technique (e.g., electrophoresis) whereby the droplets 201 may be drawn into capillary tubes 170 (e.g., into reservoirs defined by the capillary tubes 170) by capillary force attraction of the tube, which may be lined with a hydrophilic material or otherwise provided with a hydrophilic inner surface. As shown in FIG. 7, in an exemplary aspect, a plurality of capillary tubes 170, which may be held in a support 175, are filled with a matrix 171 that may comprise a porous polymer, for example, which permits movement of nucleic acid 300 that may be contained in the droplets 201. In an exemplary aspect the tubes 170 may be made of glass, for example, or other naturally hydrophilic material, such that the drops 201 are attracted to the tip of the capillaries 170 placed adjacent to the drops 201 when the EWL 20 is clamped to the capillary tube support 175.

Conventional capillary electrophoresis devices use electro-injection of DNA to introduce a plug of DNA into the small diameter of a glass capillary tube. To initiate electro-injection, the loading end of a capillary is immersed into a liquid sample containing nucleic acid. The sample is in contact with an electrode and the matrix on the distal end of the capillary is in contact with another electrode. A voltage may be applied, for example, about 1500 volts, between the electrodes such that the negatively charged nucleic acid is attracted to the distal end of the capillary tube.

Electro-injection may concentrate most of the nucleic acid from the sample liquid into a small band inside the tip of the capillary tube. After electro-injection, capillary electrophoresis can begin, which uses much higher voltages applied between the electrodes, for example, about 30,000 volts. This process can be very inefficient because the DNA sample volume into which the capillary tube is inserted typically ranges from approximately 5 microliters to approximately 20 microliters. However, only about 0.1 microliter of that volume is electro-injected into the capillary tube, i.e. about 99% of the DNA sample is wasted. This waste is a result of the need for high resolution of electrophoresis separation of small nucleic acids from larger ones. If the electro-injection spans over too long of a time period (e.g., over about 20 seconds), the nucleic acid may accumulate in a relatively long section (band) of the capillary tube, which may result in poor resolution at the detection end of the capillary tube. On the other hand, if the electro-injection time period is short (e.g., about 20 seconds or less), the acid may accumulate in a band that is relatively short, resulting in a relatively high resolution at the detection end. However, for short injection times, nucleic acid is collected from a relatively small volume of sample, typically about 0.1 microliters, for example. If the total sample volume ranges from about 5 microliters to about 20 microliters, the injection efficiency is very low.

Using the devices and methods according to aspects of the invention, a 0.1 microliter volume of DNA could be divided via electro-wetting, for example via the exemplary embodiments described herein, and delivered to the capillary tube. In contrast to the conventional approaches, therefore, the sample volume is approximately the same as the injection volume such that wasted sample liquid may be substantially eliminated and reagent costs may be reduced by a factor of almost 100.

According the exemplary embodiment of FIG. 7, the electrode 75 in the second substrate 60 of the EWL 20 may be the electrode utilized for electro-injection. That is, the droplets 201 may be placed in electrical contact with electrode 75 in the second substrate 60 and in electrical contact with distal electrodes 172 of the capillary tubes 170 via the electrically conductive matrix 171. Thus, electro-injection may be implemented using a small liquid volume (e.g., droplet 201) of an amount (e.g., about 0.1 microliter) selected so as to match the volume typically injected into a capillary tube using conventional techniques. In this way, using some of the devices and methods according to aspects of the invention may result in potentially no loss of nucleic acid during an electro-injection process.

As exemplified in FIGS. 4-7, according to aspects of the invention, dispensing the liquid droplets 201 aligned with the predetermined locations may include moving the liquid in a direction that is substantially nonparallel to a plane defined by the two-dimensional movement of the liquid through the EWL 20. For example, in the above-described embodiments, during dispensing, the liquid droplets 201 move in a direction that is substantially perpendicular to the plane of movement of the liquid through the EWL 20 during the positioning and aligning of the liquid.

It is envisioned that the electrowetting dispensing devices according to aspects of the invention, such as the EWL 20 described above, could be configured as a stand-alone device, like a multi-tip pipettor, for example, as a component of a device, like a liquid handling mechanism within an instrument, or as part of an overall system that includes fluid handling between differing devices. An example of such a system is illustrated in FIG. 8.

Figure 8:
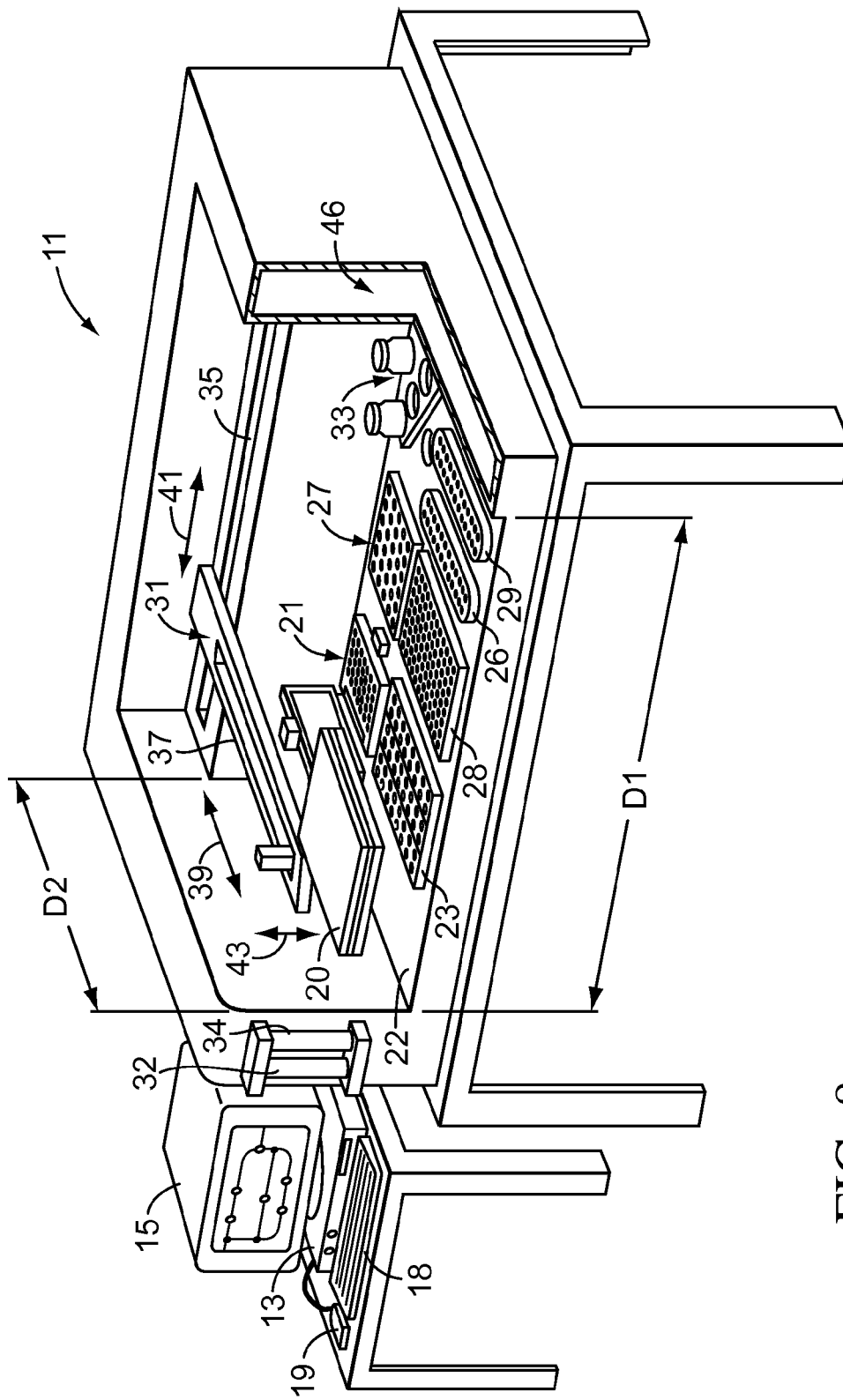
FIG. 8 is a schematic, perspective view of an exemplary embodiment of a biological analysis workstation.

FIG. 8 shows an electrowetting dispensing device, such as the EWL 20, described in the embodiment of FIG. 1, incorporated in an automated biological analysis workstation 11. Workstation 11 can include a computer 13 with a CRT monitor 15, a keyboard 18 and a mouse device 19. The computer 13, CRT display 15, mouse 19, and keyboard 18 may be hardware components of a control system with an operator interface for programming the workstation to perform desired activities including, for example, liquid handling by the EWL 20. Not illustrated in FIG. 8 is the connection between the EWL 20 and the computer 13 or between the EWL 20 and a controller, for example like controller 30 described in FIG. 1, for providing power to the electrodes of the EWL 20. However, those skilled in the art would understand that such connections are envisioned for controlling the EWL 20 and are considered within the scope of the invention.

By way of example only, the workstation could be configured to perform biological analysis comprising DNA sequence detection. To this end, the workstation 11 may include a thermal cycling station 21 with an automatically activated heated lid and real-time detection, a sample preparation station 23, a sample storage station 28, a titer plate station 27 for automatically loading a titer tray into the thermal cycling station 21, a reagent storage 33, and wash stations 26 and 29. The various stations may be arranged on a work surface 22 with width D1 and depth D2. A portion of the workstation at region 46 is shown cut away in FIG. 8 to better illustrate the components in the work area. For thermal cycling station 21 and titer plate station 27, various kinds of drives, such as, for example, motor and pneumatic drives can be used to selectively position the titer tray in and out of the thermal cycler block and to selectively close and open the thermal cycler lid.

In an exemplary aspect, a linear actuator system 31 may be utilized to move the EWL 20 over the different stations for loading liquids from containers at the various stations and dividing and dispensing smaller volumes of the liquids at the same or other stations. Liquids can also be pumped to the EWL by pumps 32 and 34. Linear actuator system 31 can be configured to move in the direction of arrow 41 along track 35. The EWL 20 can move in the direction of arrow 39 along arm 37. The EWL 20 could be translated vertically in the direction of arrow 43 so that the linear actuator system 31 can provide a cartesian XYZ placement of the EWL 20 to anywhere on the work surface 22 of workstation 11.

According to exemplary aspects, it is envisioned that the EWL 20 of the workstation 11 could be rinsed and reused numerous times to perform liquid positioning and/or dispensing operations.

FIGS. 9-13 illustrate further exemplary embodiments of dispensing devices and methods for use in positioning and dispensing liquid to a testing platform for biological analysis. As shown in the partial perspective view of FIG. 9, a dispensing device 500 may comprise a first substrate which may be in the form of a routing plate 501 (e.g., an electrowetting loader card), for example, and a second substrate, which may be in the form of a nozzle plate 502, for example. As will be explained in more detail below, the routing plate 501 may be configured to employ electrowetting so as to take an input volume of liquid (including multiple differing types of liquid), divide the liquid into smaller portions (e.g., volumes on the order of microvolumes or nanovolumes) of liquid, and position the liquid at predetermined locations along the plate 501. In an exemplary aspect, the routing plate 501 is configured to align portions of liquid to be dispensed with predetermined locations on the routing plate 501 that are substantially aligned with nozzles 520 on the nozzle plate 502.

The nozzle plate 502 may be configured so as to receive the smaller portions of liquid from the routing plate 501 via electrowetting and to express those smaller portions of liquid so as to dispense them to a testing platform for biological analysis. The testing platform may include, for example, a microscope slide, a titer plate, capillary tubes, or other testing platforms. In an exemplary aspect, the nozzles 520 of the nozzle plate may express the liquid so as to spot the liquid to a testing platform. In a further exemplary aspect, the nozzles 520 may be configured so as to receive a small volume of liquid from the routing plate 501 and to hold that small volume until additional small volumes of liquid have been positioned by the routing plate. The liquid held b the nozzles could then be expressed to a testing platform when the additional small volumes positioned in the routing plate are drawn into the nozzles.

It should be understood that for practical reasons the illustrations of FIGS. 9-13 are partial views due to the relatively high density (including ultra-high density) applications that are envisioned (e.g., for dispensing to 96-, 384-, 768-, 1536-, 3072-, 6144-, 12,288-, or 24576- and higher number well formats in the case of dispensing to titer plates.). By way of example, it may be possible to fabricate the dispensing device such that the nozzle plate includes as many as 400,000 nozzles arrayed across the surface of an area approximating 3"×5".

Figure 9:
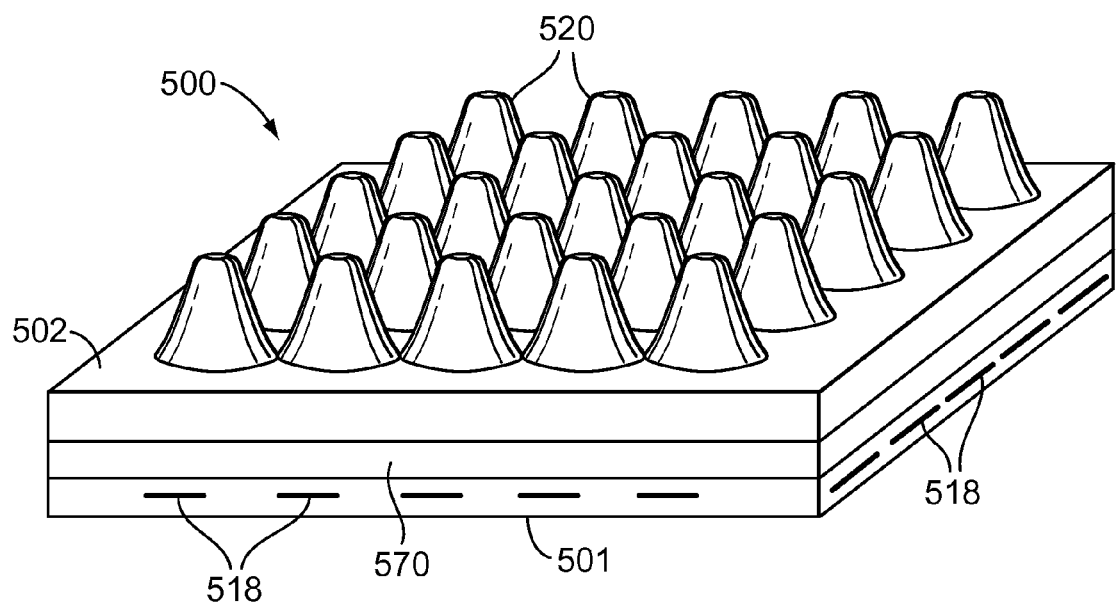
FIG. 9 is a schematic, perspective view of another exemplary embodiment of a dispensing device according to an aspect of the invention.

The dispensing device of FIG. 9 thus relies on electrowetting to divide and position an input volume of liquid via the routing plate 501 and to draw the smaller, divided portions of liquid into nozzles 520 of the nozzle plate 502 for expressing to a testing platform. The routing plate 501 and nozzle plate 502 can be positioned relative to one another to create a chamber 570 for moving and dividing the liquid along the routing plate 501 via electrowetting. For example, according to some aspects, the routing plate 501 and nozzle plate 502 may be separated from each other by a distance ranging from about 0.1 millimeters to about 10 millimeters, for example the distance may be about 1 millimeter. In an exemplary aspect, the chamber 570 formed between the routing plate 501 and nozzle plate 502 may have a volume so as to minimize evaporation of the liquid, especially in the case of smaller liquid portion/higher density applications (e.g., smaller volumes of liquid being dispensed to a larger number of locations to a testing platform).

The routing plate 501 and nozzle plate 502 may be sealed together in a manner similar to the first and second substrates 25, 60 described with reference to FIGS. 1 and 2. For example, sealing mechanisms, such as, for example, adhesive (e.g., double-sided tape), a polymer gasket, metallic seals, and/or other mechanisms capable of providing a seal, may be provided along the edges of the plates and used to secure the plates together in a spaced relationship along the edges of the plates.

Thus, according to an exemplary aspect, the routing plate 501, nozzle plate 502, and sealing mechanism may together form a housing having an interior surface, for example, a surface facing chamber 570. At least one interior surface portion of the housing may be configured so as to be electrically conductive. For example, in an exemplary aspect, at least one interior surface portion may comprise a dielectric material covering an electrical conductor.

According to an exemplary embodiment, all of the internal surfaces of the device 500, e.g., all of the surfaces coming into contact with the liquid, such as, for example, the inner surface of the routing plate 501, the inner surface of the nozzle plate 502, and the inner surfaces of the nozzles 520 (which may define nozzle reservoirs), may be configured to be hydrophobic. The routing plate 501 and the nozzle plate 502 may contain electrodes (e.g., electrodes 518 in routing plate 501, as shown in FIG. 9) or may otherwise be configured such that an electric potential may be applied to each plate so as to selectively cause inner surface portions of the plates to become wettable (e.g., hydrophilic) by altering (e.g., reducing) the contact angle between the liquid and the inner surface portion with which the liquid is in contact.

More specifically, in an exemplary aspect, an electric field associated with the routing plate 501 may be controlled so as to move an amount of input liquid along the routing plate and divide the liquid into individual portions to be dispensed. In other words, by controlling an electric field, the wettability of various surface portions on the routing plate 501 may be altered so as to move, position, and/or divide liquid within the chamber 570. During the positioning/dividing steps taking place along the routing plate 501, the nozzle plate 502 may be kept in an electrically charged state such that the inside surfaces of the nozzles 520 remain hydrophobic and liquid is repelled from entering the nozzles 520. Once the individual portions of liquid to be dispensed are positioned at predetermined locations along the routing plate 501, for example, in alignment with openings to the nozzles 520, the electric field acting on the plates 501 and 502 may be controlled such that the individual portions of liquid will be drawn from the predetermined locations along the routing plate 501 and into the respective nozzles 520 via electrowetting and capillary action. By way of example, the power and ground states of the plates 501 and 502 may be switched so as to cause the inner surfaces of the routing plate 501 in contact with the liquid to become hydrophobic and the inner surfaces of the nozzles 520 to become hydrophilic, thereby repelling liquid from the routing plate 501 and drawing the liquid into the nozzles 520 (e.g., into the reservoirs defined by the inner surfaces of the nozzles).

With reference to FIGS. 10A-10D, exemplary steps of dividing, positioning, and drawing liquid so as to be ready for dispensing using an embodiment of a dispensing device 600 comprising a routing plate 601 and a nozzle plate 602 are schematically illustrated. The views of FIGS. 10A-10D are side, cross-sectional views of the dispensing device 600; the cross-section of the routing plate 601 shown in FIGS. 10A-10D is taken along the line 10-10 illustrated in FIG. 12A. Therefore, in the view shown in FIGS. 10A-10D, the direction of movement of the liquid along the routing plate 601 is shown in only one dimension. It should be understood, however, that movement along the routing plate 601 is in two dimensions. Further, as will be seen, in an exemplary aspect, dispensing through the nozzles 620 may be in a direction substantially nonparallel (for example, perpendicular) to a plane defined by the two-dimensional movement of liquid along the routing plate 601. Details of how the input liquid may be divided and moved along the routing plate 601 in an exemplary aspect are provided below in the description of FIGS. 11 and 12.

Figure 10A:
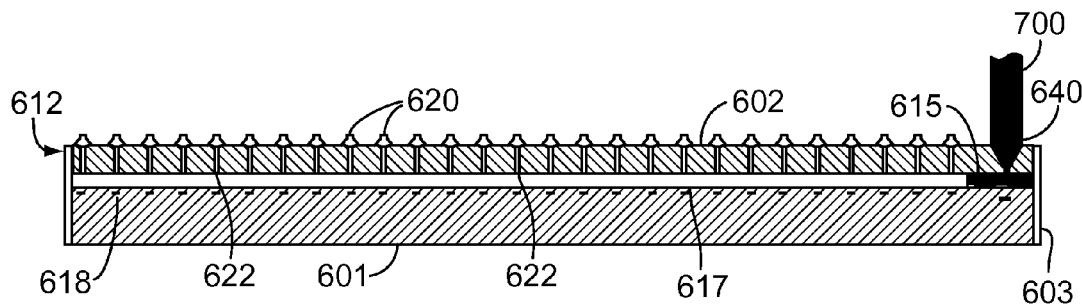
FIGS. 10A-10D are schematic side views of another exemplary embodiment of a dispensing device and various exemplary steps for positioning liquid.

In FIG. 10A, a liquid 700 to be dispensed is introduced through an input port 640 provided in the dispensing device 600. The input port 640 may be in flow communication with a main filler rail 615 provided in routing plate 601. In the cross-sectional views of FIGS. 10A-10D, the main filler rail 615 extends in a direction into the plane of the drawing sheet. The main filler rail 615 may be a surface underlain by lithographically formed electrodes, for example. In an exemplary aspect, the main filler rail may define a channel formed in the surface of the routing plate 601.

In a manner similar to that described with reference to FIG. 2, the main filler rail 615 can be configured such that it is capable of controlling the movement of the input liquid from the input port 640 along the filler rail 615 (e.g., in a direction into the plane of the drawing sheet) via electrowetting. For example, the routing plate 601 may be provided with electrodes 618 that may be controlled as desired so as to position and divide liquid supplied to the filler rail 615. In the exemplary step of FIG. 10A, the input liquid 700 is moved from the input port 640 so as to substantially fill the main filler rail 615 that runs along a side 603 of the routing plate 601.

Figure 10B:
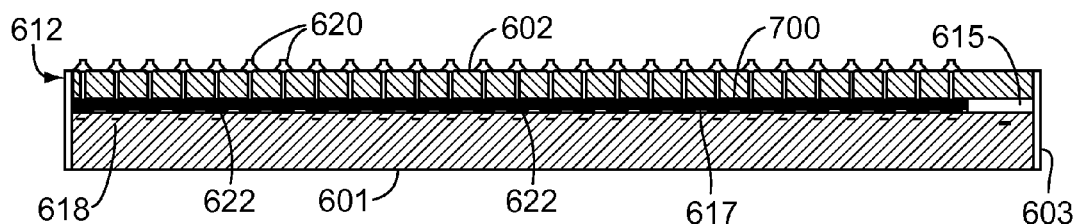

Referring to FIG. 10B, once the main filler rail 615 has been substantially filled with liquid, smaller portions of the liquid in the main filler rail 615 may be drawn, again via electrowetting, into a plurality of side arms 617, which may comprise channels, defined by the router plate 601. The side arms 617 extend in a direction substantially perpendicular to the main filler rail 615 so as to form a plurality of substantially parallel rows. Due to the side, cross-sectional views of FIGS. 10A-10D, only one such side arm 617 can be seen. As can be seen in the exemplary embodiment of FIG. 10B, the side arms 617 of the routing plate 601 may be positioned such that each arm 617 is substantially in alignment with a row of nozzles 612 of the nozzle plate 602.

Figure 10C:
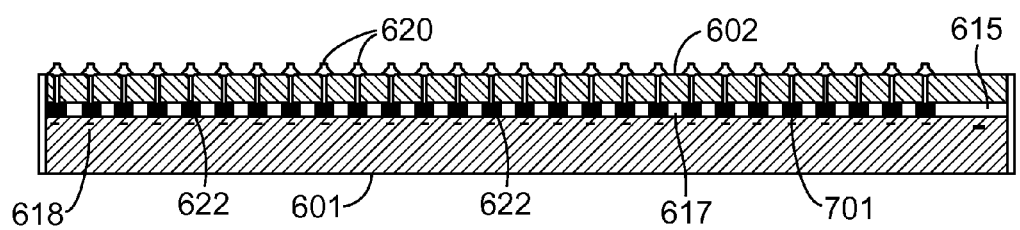

Once the side arms 617 of the routing plate 601 have been filled with liquid and the main filler rail 615 has been emptied, the electric field of the routing plate 601 may be controlled so as to divide the liquid filling each of the side arms 617 into a plurality of individual portions of liquid 701 via electrowetting. FIG. 10C illustrates the liquid 700 in an arm 617 being divided into individual portions of liquid 701 for dispensing. As can be seen in the exemplary step of FIG. 10C, individual portions of liquid 701 may be formed at predetermined locations on the routing plate 601 that are in substantial alignment with respective nozzles 620 of the nozzle plate 602.

Figure 10D:
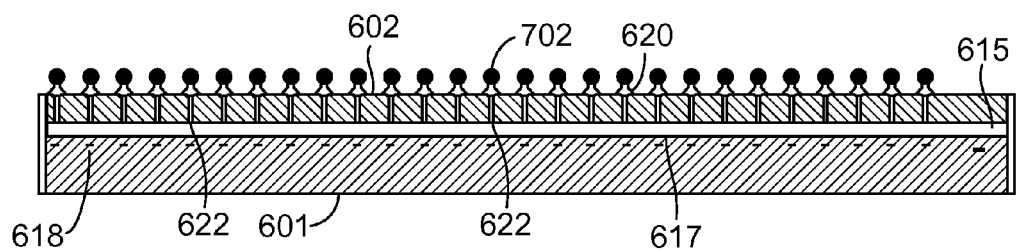

Once the liquid has been divided into the individual portions 701 to be dispensed and aligned with the nozzles 620, electrowetting may again be utilized to draw the individual portions of liquid 701 from their respective predetermined locations on the routing plate 601 and into respective openings 622 leading to the nozzles 620. As shown in FIG. 10D, by drawing the partitioned liquid 701 from the routing plate 601 and into the nozzles 620 via electrowetting, the individual portions of liquid 701 may be expressed through the nozzles 620 such that they form a droplet 702 or the like held by capillarity at the tip of each nozzle 620. The dispensing device 600 may then be brought into alignment with a testing platform, such as, for example, a titer plate, a microscope slide, or the like, and brought into contact with predetermined locations on such a platform to dispense (e.g., spot) the droplets 702 onto the predetermined locations on the testing platform so that biological analysis can be performed. In an exemplary aspect, as illustrated in FIG. 10D, the individual droplets 701 of liquid are dispensed through the nozzles 620 in a direction that is substantially perpendicular to the two-dimensional plane of movement of the liquid along the routing plate 601.

The volume of each droplet 702 that the nozzles 520 dispense may be substantially the same as the volume of each respective individual portion of liquid 701 divided on the routing plate 601. Alternatively, it may be advantageous to provide the nozzle reservoir with a volume that is about twice the volume of the droplet expressed from the nozzle.

In this manner, the nozzle may function as a holding volume while a second volume (e.g., individual portion) for dispensing is being positioned along the routing plate. When the second volume (e.g., individual portion) is moved into the nozzles, the first volume (e.g., individual portion) would be expressed from the nozzle.

Figure 11:
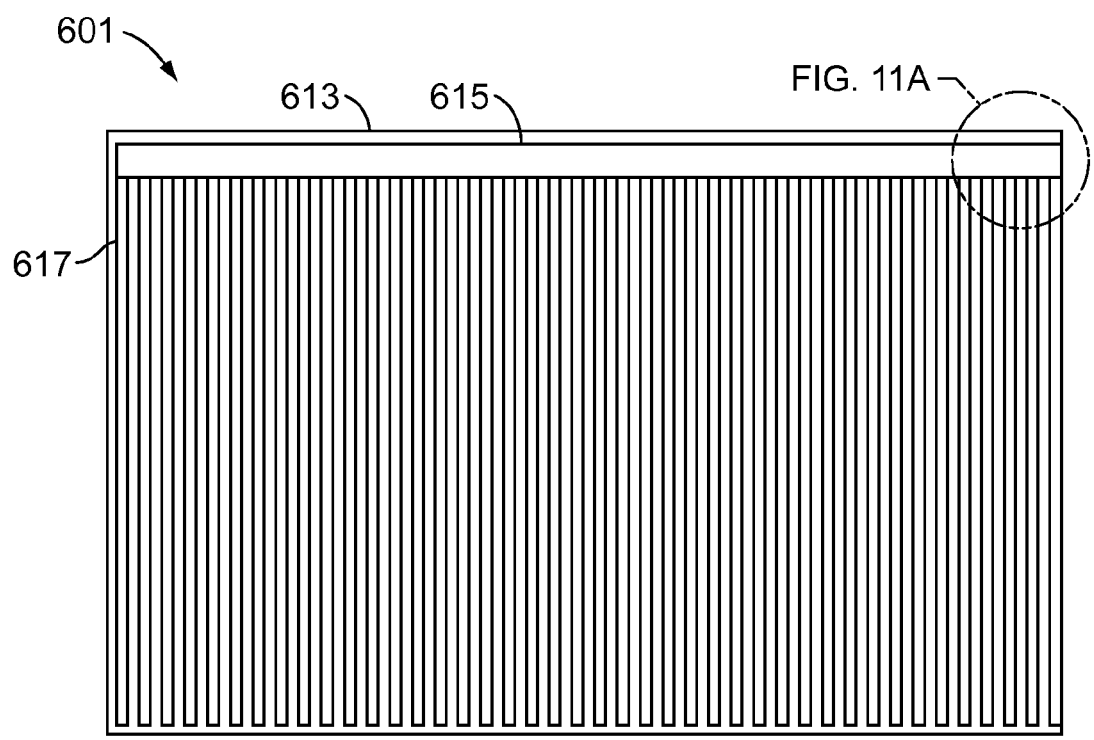
FIGS. 11 and 11A are a plan view of an exemplary embodiment of a routing plate in accordance with an aspect of the invention.
Figure 11A:
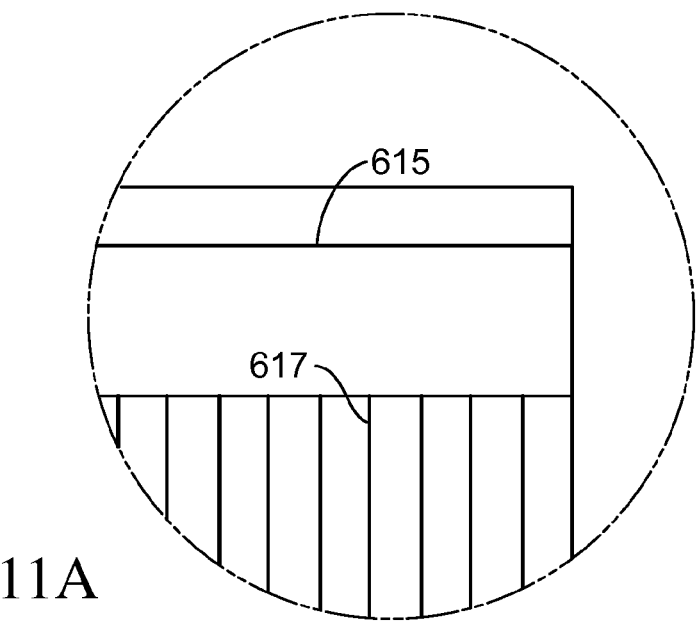

FIG. 11 shows a schematic, top view of an exemplary embodiment of the routing plate 601 that may be used with a dispensing device as described in FIGS. 9 and 10. FIG. 11A is a blown-up view of a section of the routing plate 601 of FIG. 11. The routing plate 601 may be substantially in the form of a card-like structure having a main filler rail 615 extending along an edge 613 of the plate 601. A plurality of side arms 617 may extend from the main filler rail 615, for example, in a substantially perpendicular direction to the rail 615. As illustrated in FIGS. 10-12, the rail 615 and arms 617 may be defined as pathways on a surface of the plate 601, for example pathways defined by surface portions on the plate 601 underlain with electrodes. According to an exemplary aspect (not shown), the rail 615 and arms 617 may be formed as channels in the plate 601. The arms 617 may be in flow communication with the rail 615. The main filler rail 815 may be configured so as to be capable of containing a volume of liquid substantially equal to the total volume of liquid that the arms 617 are capable of containing. By way of example, the main filler rail 615 may be configured to contain an amount of liquid ranging from about 0.1 microliter to about 10 milliliters. According to one exemplary embodiment, to use the device 600 to fill a 1536-well titer plate with 4 microliters of liquid per well, the rail 615 should be configured so as to contain at least 6.144 milliliters of liquid.

According to an exemplary aspect, and not illustrated in FIGS. 11 and 11A, the routing plate 601 may comprise an array of electrodes that are positioned in substantially along the filler rail 615 and arms 617 such that microfluidic pathways are formed along the filler rail 615 and arms 617. In other words, by selectively activating the electrodes, surface portions on the routing plate 601 corresponding to those electrodes may be altered so as to become more or less wettable (e.g., exhibit hydrophobic characteristics or hydrophilic characteristics) so as to provide precise control over the movement of liquid along the rail 615 and the arms 617. In an exemplary aspect, the microfluidic pathways (e.g., the rail 615 and the arms 617) are underlain by lithographically defined arrays of electrodes.

Numerous techniques may be used to provide the electrodes in the routing plate and/or to otherwise configure the routing plate such that it is capable of achieving electrowetting. For example, one such technique may include implanting electrical pads in a substrate covered with a hydrophobic insulator layer, for example, in a manner similar to that described for first substrate 25 of FIG. 1.

Another technique may include fabricating the electrodes positioned underneath the microfluidic pathways of the routing plate from a sequence of steps that has been used for micro-electronic devices, such as multi-chip modules, for example. For references which describe the steps used for micro-electronic devices and multi-chip modules, reference may be made to http://www.cpmt.org/past_trans/cpmtb_toc_9502.html, for example. In accordance with this technique, electrodes may be formed using a series of steps involving deposition of a suitable conductive material. Such conductive materials may include, for example an indium/tin/oxide alloy, aluminum, gold, and/or other conductive materials. The conductive material may then be patterned with a subtractive process, such as, for example, wet chemical etching or a dry process, such as plasma etching, for example. For example, a photo-masking process may be employed on top of a deposited conductive material, followed by a subtractive etching process as described above, in order to remove unwanted conductive material and leave electrodes in place. After performing the subtractive process to pattern the conductive material into an array of electrodes, a thin layer of a dielectric material may be applied. Suitable dielectric materials may include, for example, polymers, or oxides and/or nitrides having high dielectric constants. The layer thickness may be a function of the dielectric constant of the material. For example, the higher the dielectric constant, the thinner the layer. According to an exemplary aspect, the dielectric material may be applied in a layer having a thickness ranging from about 1 micrometer to about 10 micrometers.

The layer of dielectric material may be applied so as to isolate the conductive patterns so as to form the desired electrode positioning (e.g., array) relative to the routing plate surface. First, the electrode structure may be formed using the deposition and subtractive processes described above. The dielectric material may then be applied as a substantially continuous coating over the formed electrodes. For example, the dielectric material may be applied via spin coating, sputtering, chemical vapor deposition, plasma enhanced chemical vapor deposition, and/or other deposition techniques. The series of steps described above may be repeated as needed to achieve the desired granularity of the electrodes. The term granularity is used herein to describe the size of the individual electrodes. For example, a high granularity refers to a relatively high number of individual electrodes per square unit of surface area.

In order to make the formed electrodes independently chargeable, each of the electrode layers may be interconnected to routing layers of conductors that terminate at a series of edge connection points. An external electrical control system (not shown) may be connected to those connection points and can be used to individually activate the electrodes in any series and/or sequence as needed to move and/or divide the liquid along the routing plate. In other words, in a manner similar to that described with reference to FIGS. 2 and 3, the charge of the electrodes may be controlled so as to cause corresponding surface portions of the routing plate to exhibit hydrophobic characteristics or hydrophilic characteristics in order to divide and move liquid over the routing plate surface.

FIGS. 12A-12F show a plan view of the routing plate of FIG. 11 and exemplary steps for how liquid supplied to the routing plate 601 may be moved along the filler rail 615 and arms 617 of the routing plate 601 and divided into individual portions for dispensing from the nozzles of a nozzle plate. The surface of the routing plate 601 illustrated in FIGS. 12A-12F is the surface in contact with the liquid and facing the nozzle plate.

Figure 12A:
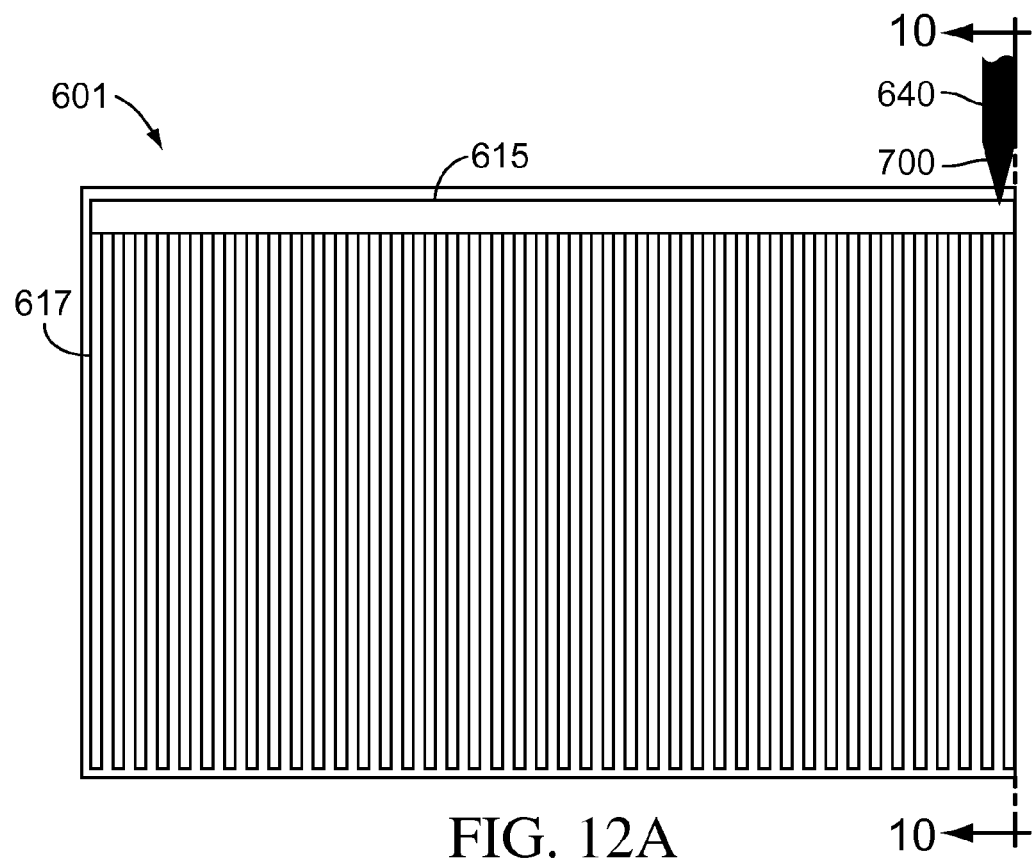
FIGS. 12A-12G schematically illustrate various exemplary steps for positioning and dividing liquid along the routing plate of FIG. 11.

With reference to FIG. 12A, liquid 700 to be dispensed is first introduced to the routing plate 601 into the main filler rail 615. As was described with reference to FIG. 10A, the liquid 700 may be introduced, for example, via a port 640 in flow communication with the filler rail 615, in a direction substantially perpendicular to the plane of the routing plate 601 (not shown in the figures). In a manner similar to that described with reference to FIG. 2A, the liquid 700 may be prevented from moving along the filler rail 615 by controlling the electric charge of an array (e.g., a two-dimensional array) of electrodes underlying the filler rail 615 so as to make the surface of the filler rail 615 in contact with the liquid substantially hydrophobic, thereby repelling the liquid.

Figure 12B:
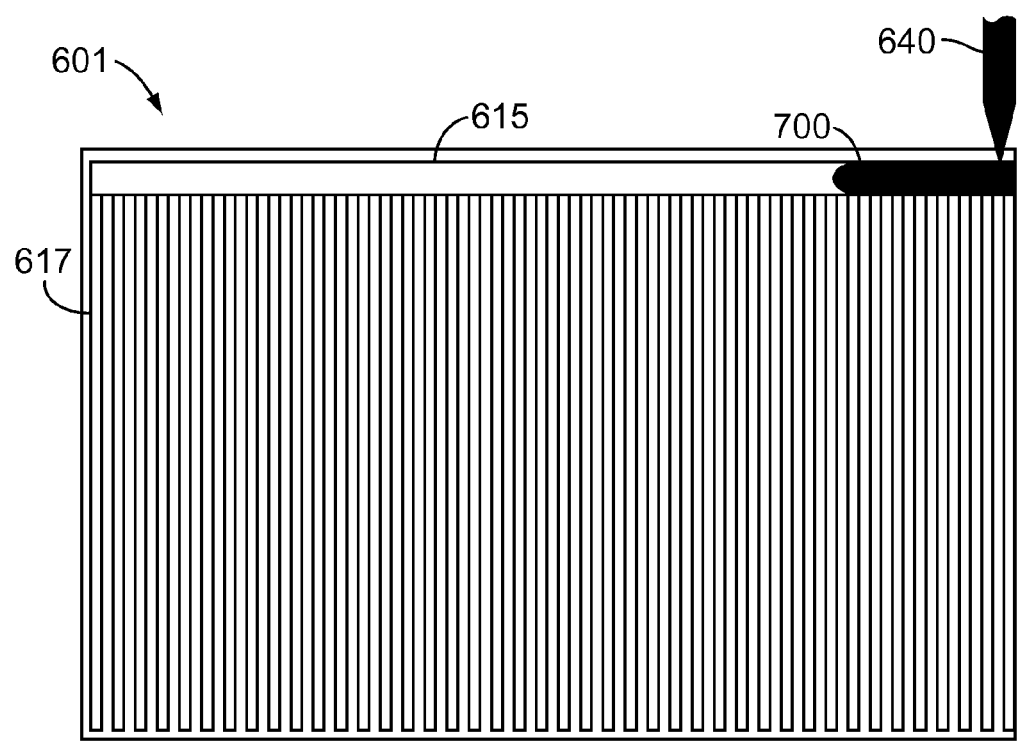
Figure 12C:
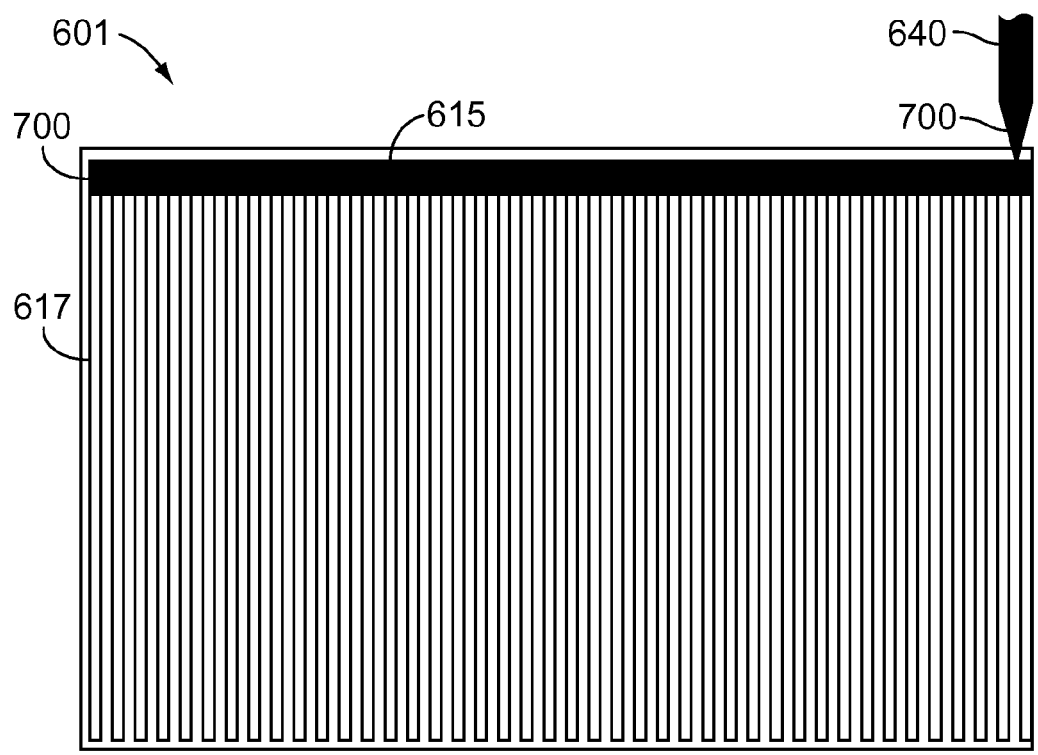

When it is desired to fill the filler rail 615, the electric charge of an array of electrodes associated with the filler rail 615 may be controlled so as to move the liquid 700 from the input port 640 and along the rail 615. FIG. 12B shows an example of the liquid 700 progressing from its input position in the upper corner of the routing plate 601 along the filler rail 615. FIG. 12C illustrates the main filler rail 615 being completely loaded with liquid 700.

Figure 12D:
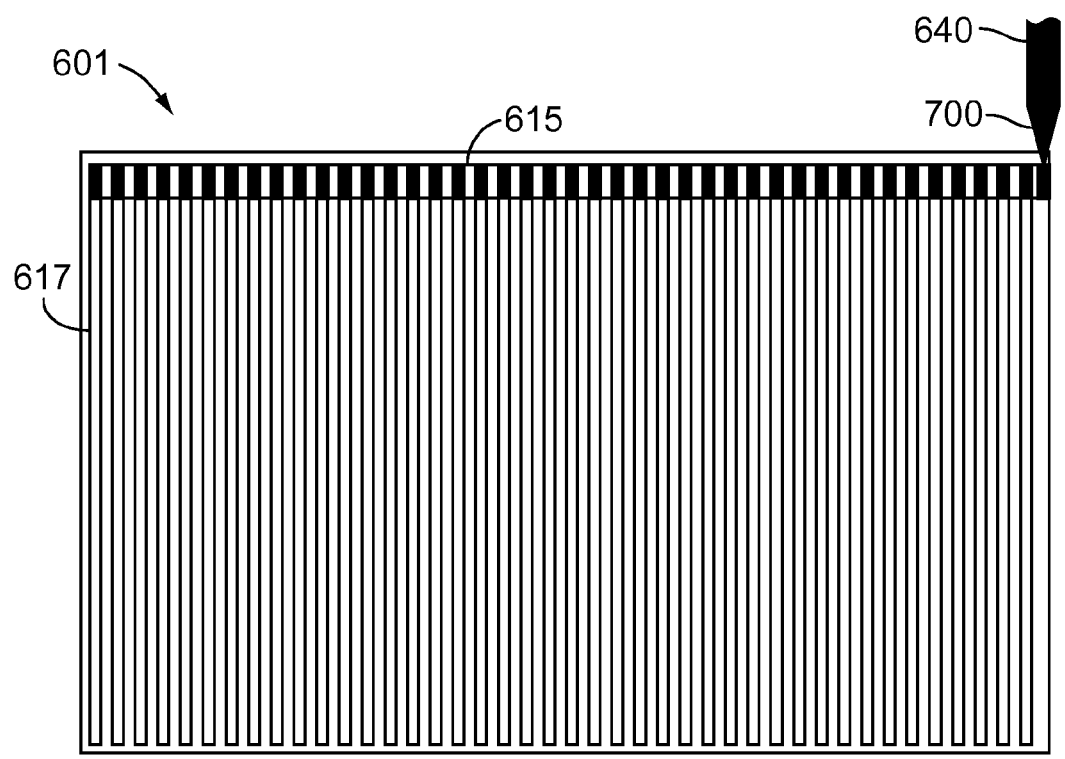

Once the main filler rail 615 is completely loaded with liquid 700, as shown in FIG. 12C, the array of electrodes on the routing plate 601 may again be controlled so as divide the liquid in the filler rail 615 into a plurality of smaller, individual portions that are substantially separated from one another along the filler rail 615 and aligned with respective arms 617. FIG. 12D illustrates this exemplary step, wherein the electrodes of the routing plate 601 are selectively activated so as to partition the liquid 700 in the main filler rail 615 into a plurality of separate portions that are in substantial alignment with the plurality of arms 617. In other words, electrodes corresponding to surface portions of the filler rail 615 are selectively turned off so as to cause those surface portions to become hydrophobic, thus repelling the liquid and partitioning the liquid into portions illustrated in FIG. 12D. The partitioned portions of liquid in FIG. 12D collect over surface portions of the filler rail 615 corresponding to activated electrodes. The volume of liquid 700 in each of the partitioned portions in FIG. 12D may be substantially equal to the volume of each respective arm 617, such that each partitioned portion of liquid can substantially fill a respective arm 617.

Figure 12E:
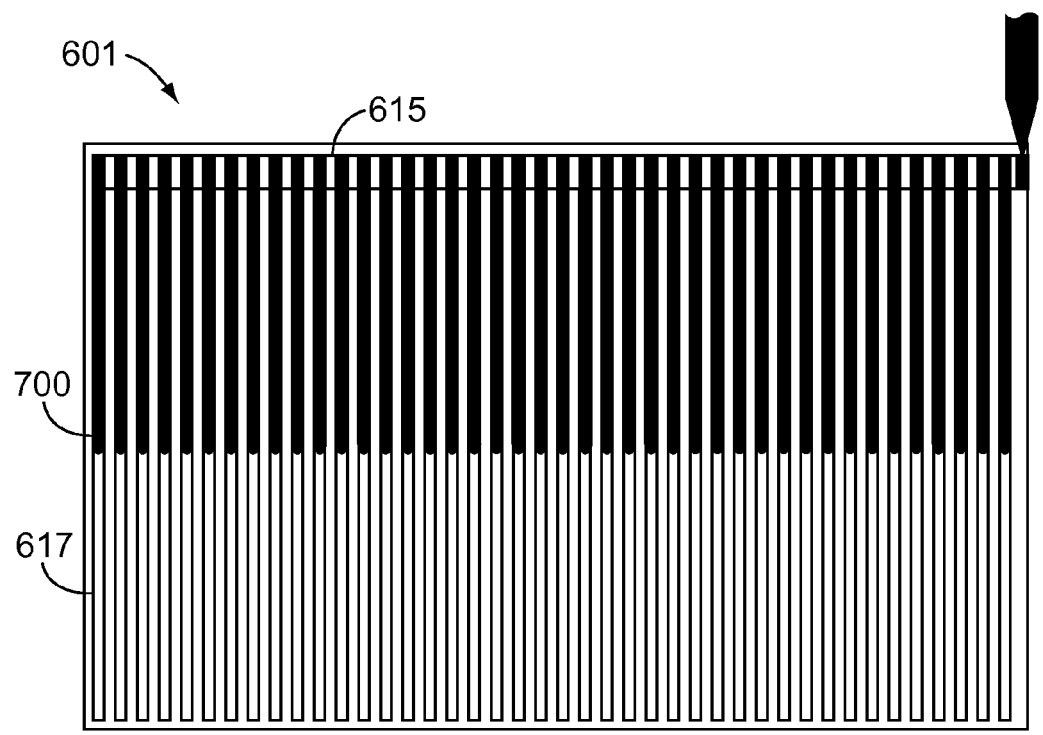
Figure 12F:
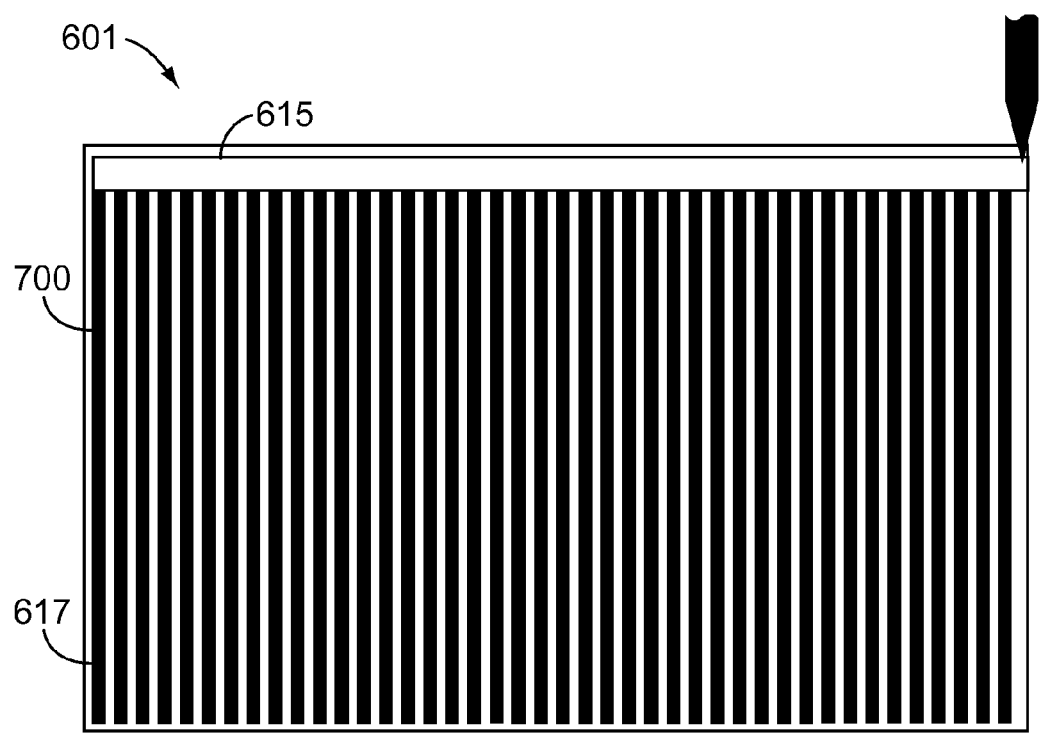

An exemplary step of filling the arms 617 with the liquid 700 is illustrated in FIG. 12E. By selectively activating electrodes aligned along the arms 617, the partitioned liquid in the filler rail 615 may be drawn into the arms 617 and away from the filler rail 615. As the liquid 700 progresses from the filler rail 615 into the arms 617, eventually all of the liquid 700 is drained from the filler rail 615 and is contained in the arms 617, as illustrated in FIG. 12F. Thus, as shown in the exemplary steps illustrated in FIGS. 12A-12F, liquid 700 may be moved in a two-dimensional manner along the routing plate 601 by selectively controlling the electric field acting on the liquid and thereby controlling the wettability of surface portions in contact with the liquid. Further, the liquid 700 may be divided into a plurality of smaller amounts corresponding to a plurality of substantially parallel rows corresponding to the arms 617.

Figure 12G:
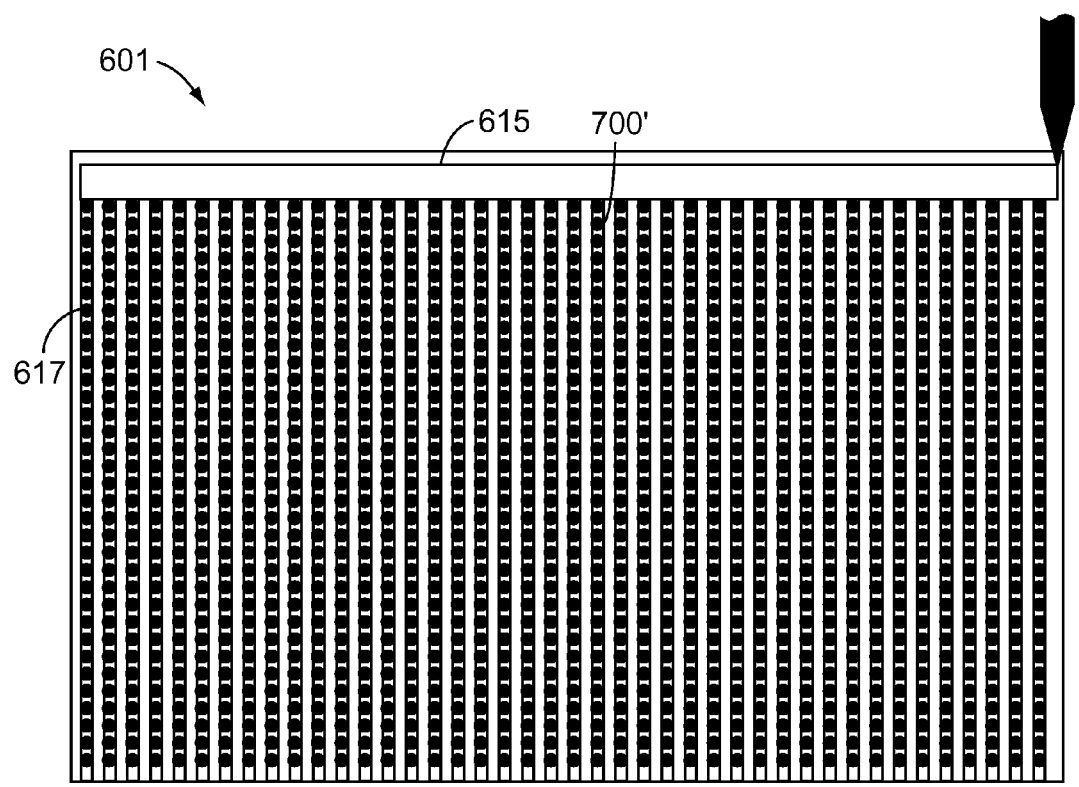

Referring now to FIG. 12G, once the liquid 700 has been moved from the filler rail 615 into the arms 617, various electrodes associated with the arms 617 can be activated so as to again divide the liquid 700 in the arms 617 into a plurality of individual portions 701 (for example on the order of a few microliters or a few nanoliters, such as, for example, ranging from about 0.01 microliters to about 100 microliters, for example about 1 microliter) aligned with a plurality of predetermined locations. In particular, according to an exemplary aspect, the electrodes may be controlled so as to cause, via electrowetting, the liquid 700 in the arms to be divided into individual portions 701 located at predetermined locations on the routing plate 601 that are aligned with respective openings leading to nozzles of a nozzle plate. FIG. 12G illustrates the exemplary step of dividing the liquid 700 aligned with the arms 617 into a plurality of individual portions 701 ready to be drawn into nozzles (e.g., into the reservoirs defined by the inner surfaces of the nozzles) of a nozzle plate, such as, for example, a nozzle plate like that shown in FIG. 10, for dispensing to a testing platform. It should be understood that the number and locations of the individual portions 701 of liquid illustrated in FIG. 12G are exemplary and that the number, location, and volume of the individual portions 701 of liquid can be controlled as desired, for example, based on the routing plate electrode configuration and/or the activation of the routing plate electrodes. The volume of individual portions of liquid may vary depending on the application. For example, the dispensing devices disclosed herein could be configured to fill wells having a volume of about 10 nanoliters in a 24,000-well format. In another example, the dispensing device could be configured to fill wells having a volume ranging from about 10 microliters to about 100 microliters in a 384-well format. It is envisioned that the dispensing devices according to aspects of the invention could be configured to dispense liquid in a relatively wide range of volumes.

As explained above, once the individual portions 701 have been established, as shown in FIG. 12G, the electrodes associated with the routing plate 601 can again be controlled, e.g., via a controller (not shown) so as to cause the routing plate surface to become hydrophobic. At the same time, the electric potential of a nozzle plate associated with the routing plate 601 could be controlled so as to cause the nozzle inner surfaces to change from exhibiting hydrophobic characteristics to exhibiting hydrophilic characteristics, thereby drawing the individual portions 701 into the nozzles via electrowetting and/or capillarity.

Thus, the routing plate embodiment of FIG. 12 permits the supplied liquid to be moved along in a somewhat bulk fashion, e.g., by volumes corresponding to the rail 615 and arms 617, prior to dividing the liquid into individual portions desired for dispensing, such as, droplets, for example. In this way, evaporation may be minimized and efficiency improved by eliminating the need to move individual droplets (or other small portions volumes desired to be dispensed) along relatively long routes prior to dispensing the individual droplets.

A variety of techniques could be employed to fabricate a nozzle plate according to an exemplary embodiment. In an exemplary aspect, it is desirable to fabricate the nozzle plate using a technique that permits an ultra-high density nozzle configuration, such as that described in the exemplary embodiment of FIGS. 13A and 13B. One such technique, for example, could include a series of steps that are known to those skilled in the art of silicon micro-machining technologies. For example, through-holes could be formed in a silicon plate using a lithographic process followed by a deep reactive ion etching (DRIE) process. DRIE is a process that utilizes the pulsing of power during a reactive ion etch process to alternately etch a hole and then coat the side walls of that hole with polymeric byproducts that protect against etching. The process allows for the formation of structures having relatively high aspect ratios. Once the through-holes have been formed, an atmospheric down-stream plasma (ADP) process can be used in conjunction with a standard lithographic process to form the nozzles. ADP is an isotropic process which can lead to the tapered shape of the nozzles.

After formation of the nozzles, the inside surface of the nozzle plate (e.g., including the inside surface of the nozzles) can be coated with a layer of hydrophobic material, such as, for example, polymeric materials and other resins that may be applied in solution where the solvent is allowed to evaporate leaving behind a film that may range from about 0.5 micrometers to about 1.5 micrometers in thickness. Other film thickness ranges are envisioned and may be selected based on the particular application. Further, the nozzles may be coated with a layer of conductive material and a layer of hydrophobic material in a manner similar to that described with reference to the wells 150 of FIG. 6.

Further information regarding DRIE can be found at http://www.microfab.de/technologies/drie.htm, and further information regarding ADP can be found at http://www.tru-si.com/frames.asp.

Figure 13A:
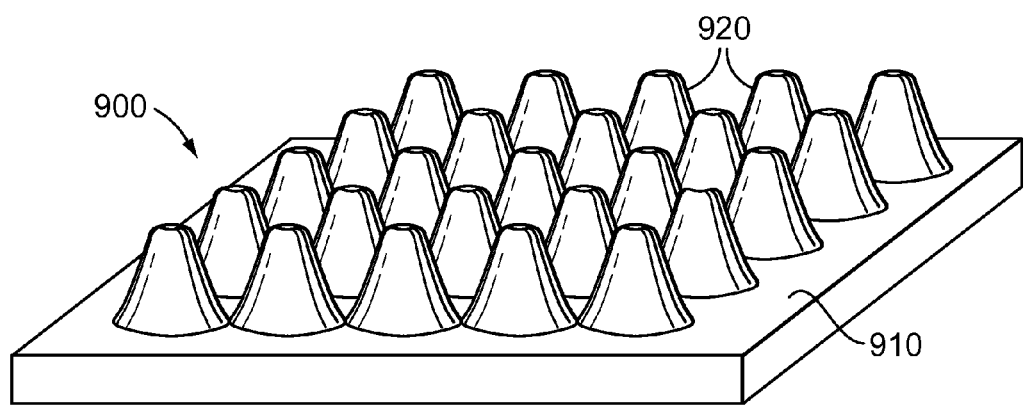
FIGS. 13A and 13B are partial, schematic perspective views of an exemplary embodiment of a nozzle plate according to an aspect of the invention.
Figure 13B:
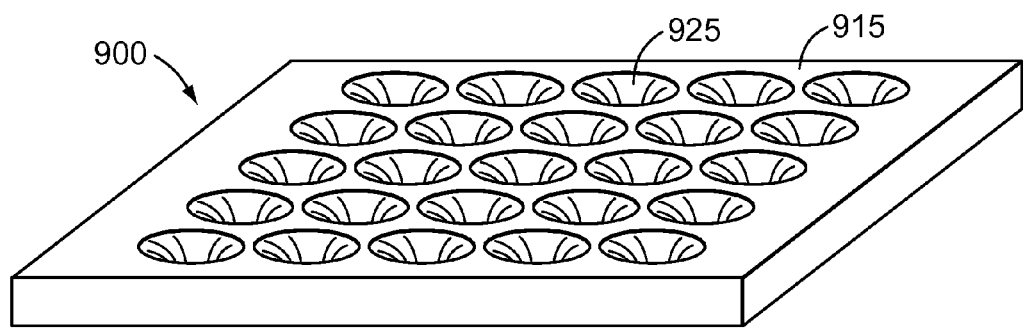

A partial view of an exemplary embodiment of a nozzle plate configuration is shown in FIGS. 13A and 13B. It should be understood that for practical reasons the illustrations are partial views due to the large number of nozzles that are envisioned for the exemplary biological analysis applications described herein. For example, as explained above, it may be possible to fabricate the nozzle plate such that there are as many as 400,000 nozzles arrayed across the surface of an area approximating 3"×5". Thus, only a small portion of a nozzle plate is illustrated in FIGS. 13A and 13B.

FIG. 13A illustrates a perspective view of a nozzle plate 900 viewed from the nozzle side 910, which is the side of the nozzle plate facing away from the routing plate. As shown, the nozzle plate 900 includes a plurality of nozzles 920 arranged in an array of rows and columns. In an exemplary aspect, the nozzles 920 would be configured so as to align with predetermined locations on a testing platform, such as with wells on a titer plate, for example. FIG. 13B illustrates the opening side 915 of the nozzle plate 900. The opening side 915 faces toward the routing plate and makes contact with the liquid to be dispensed. The opening side contains a plurality of openings 925 leading to the nozzles 920.

By way of example only, the nozzle plate 900 of FIGS. 13A and 13B may have an ultra-high density configuration and the nozzles 920 may be spaced from one another at approximately a 200 micrometer pitch. The openings of the nozzles from which the liquid is dispensed may have a diameter on the order of approximately 50 micrometers. It should be understood, however, that this nozzle plate configuration is exemplary only and that the number of nozzles, the nozzle dimensions, the spacing between the nozzles, and the nozzle arrangement may be chosen depending on the dispensing application. For example, the volume of each nozzle may be selected based on the desired volume of expressed liquid.

Figure 14:
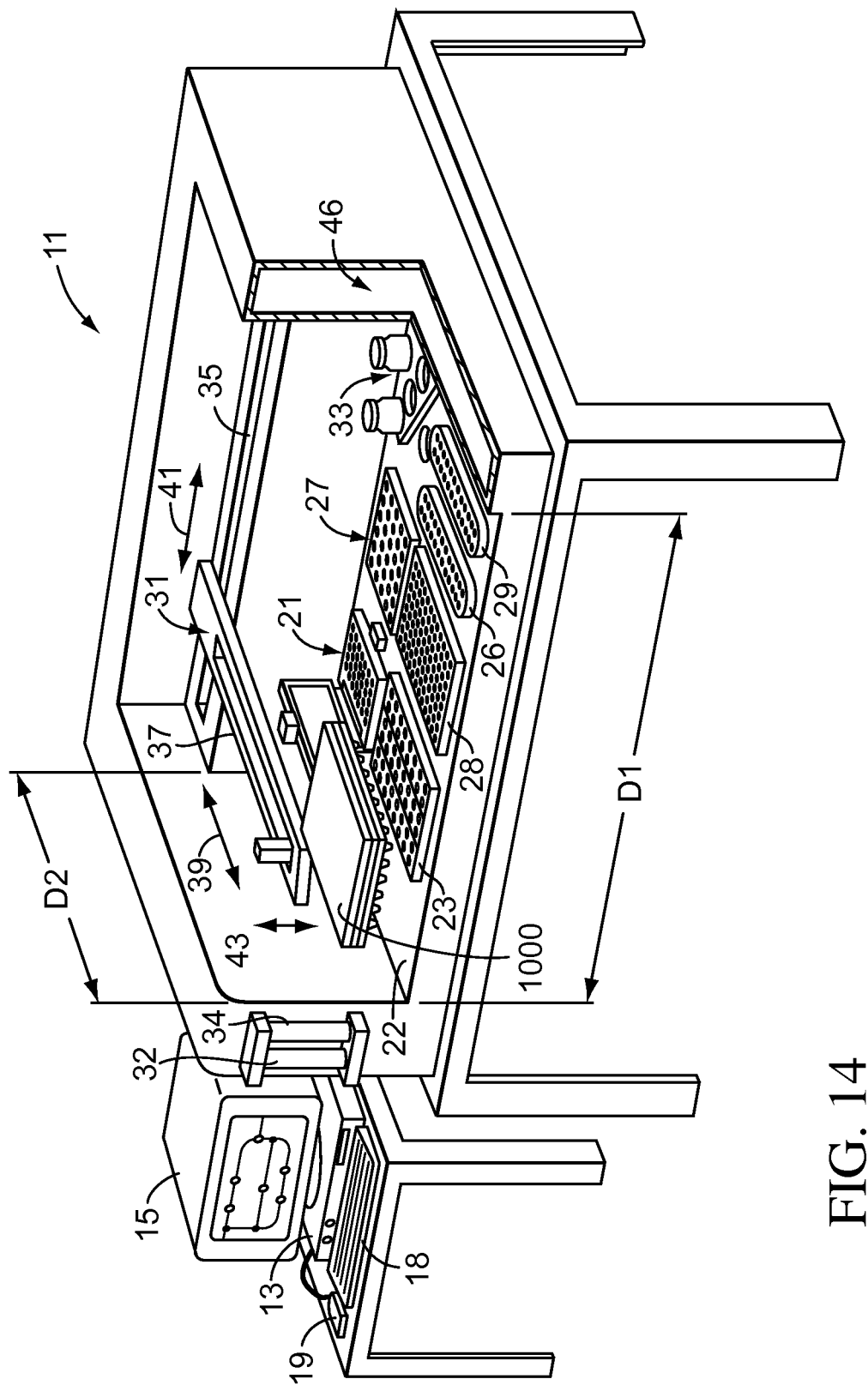
FIG. 14 is a schematic, perspective view of another exemplary embodiment of a biological analysis workstation.

As with the embodiments of FIGS. 1-7, it is envisioned that routing plate/nozzle plate dispensing device discussed with reference to FIGS. 9-13 could be configured as a stand-alone device, like a multi-tip pipettor, for example, as a component of a device, like a liquid handling mechanism within an instrument, or as part of an overall system that includes fluid handling between differing devices. Thus, as shown in FIG. 14, a routing plate/nozzle plate electrowetting dispensing device 1000 could replace the EWL 20 illustrated in FIG. 8. The dispensing device 1000 could be manipulated and function as part of a workstation system 11 in a manner similar to that described and illustrated in FIG. 8 and as described above with reference to the description of FIG. 8, with the exception that the EWL 20 of FIG. 8 is replace with the routing plate/nozzle plate dispensing device 1000.

To the extent not already described above, it should be understood that devices and methods according to the invention may include various exemplary aspects and/or features, some of which are set forth in the following. A method for dispensing liquid may include aligning the liquid with a plurality of predetermined locations corresponding to a two-dimensional array. Positioning the liquid may comprise moving the liquid, for example moving individual portions of liquid, in two dimensions. Dispensing aligned liquid may comprise moving the liquid, such as, for example, individual portions of liquid, in a direction substantially nonparallel to a plane defined by the two dimensions, for example, in a direction substantially perpendicular to a plane defined by the two dimensions. A method for dispensing liquid may comprise providing a first amount of liquid and dividing the first amount of liquid into a plurality of individual portions less than the first amount via electrowetting. Positioning liquid via electrowetting may comprise positioning each of the plurality of individual portions into respective alignment with each of the plurality of predetermined locations.

A method for dispensing liquid may comprise dividing the first amount of liquid into a plurality of substantially parallel rows of liquid. Dividing the first amount of liquid may comprise dividing the first amount of liquid into a plurality of droplets of liquid. Dividing may further comprise dividing the first amount of liquid into a plurality of individual portions each ranging from about 0.01 microliters to about 100 microliters, for example, from about 0.01 microliters to about 5 microliters, for example about 1 microliter. A method for dispensing liquid may further comprise filling openings in a substrate with the liquid prior to dispensing the liquid through the openings. During the filling, the openings may exhibit hydrophilic characteristics such that the liquid moves from predetermined locations into the openings. Further, prior to the filling, the openings may exhibit hydrophobic characteristics. Filling the openings with the liquid may comprise moving the liquid into the openings via electrowetting. Dispensing aligned liquid through the plurality of openings in a substrate may comprise dispensing the aligned liquid through a plurality of port openings.

A method for dispensing liquid may further comprise dispensing individual portions of liquid via a plurality of nozzle openings. Further, the method may comprise spotting the plurality of individual portions of liquid to a testing platform via the nozzle openings. In another aspect, dispensing the plurality of individual portions of liquid may comprise dispensing the individual portions via a plurality of port openings. The dispensing the plurality of individual portions of liquid may include dispensing the plurality of individual portions of liquid to a plurality of reservoirs. According to an aspect, the dispensing the plurality of individual portions of liquid to the plurality of reservoirs may comprise centrifuging the plurality of individual portions of liquid to the plurality of reservoirs. The plurality of individual portions of liquid into may be dispensed to a plurality of reservoirs coated with a hydrophilic material.

According to another aspect, the dispensing the plurality of individual portions of liquid to the plurality of reservoirs may comprise dispensing the plurality of individual portions of liquid via electrowetting, for example, the dispensing may comprise dispensing the plurality of individual portions of liquid to a plurality of wells in a titer plate. The reservoirs may be coated with a layer of conductive material and a layer of hydrophobic material, and the dispensing via electrowetting may comprise altering an electric potential of the reservoir such that an inner surface of the reservoir exhibits hydrophilic characteristics.

According to yet a further aspect, the dispensing the individual portions of liquid to a plurality of reservoirs may comprise dispensing the plurality of individual portions of liquid to the plurality of reservoirs via capillarity, and the reservoirs may comprise hydrophilic capillary tubes. In another aspect, the dispensing the plurality of individual portions of liquid to a plurality of reservoirs may comprise dispensing the plurality of individual portions of liquid via electrophoresis.

A method for dispensing liquid may further comprise moving aligned liquid to a plurality of reservoirs, wherein the moving comprises altering an electric potential of the reservoirs so as to cause an inner surface of the reservoirs to exhibit hydrophilic characteristics.

A device for positioning liquid to be dispensed may comprise, in an exemplary aspect, a first substrate and second substrate separated from the first substrate, the second substrate defining at least one opening therethrough, the at least one opening being configured to permit passage of an amount of liquid to be dispensed therethrough. The device may further comprise a chamber between the first substrate and the second substrate, the chamber being configured to contain liquid for dispensing. A controller may be configured to control an electric field acting on the liquid in the chamber so as to move a portion of the liquid in the chamber into alignment with the at least one opening and to dispense the portion of the liquid through the at least one opening.

According to additional exemplary aspects, the at least one opening may comprise a plurality of openings. The at least one opening may also comprise an inner surface configured to exhibit hydrophobic characteristics prior to dispensing the liquid through the opening. The inner surface of the at least one opening may be configured to exhibit hydrophilic characteristics during the dispensing of the liquid through the opening. The second substrate may define a plurality of nozzles and the plurality of openings may comprise nozzle openings. The plurality of nozzles may be configured to dispense a plurality of individual portions of the liquid to a titer plate. The controller may be configured to control the electric field so as to move a plurality of individual portions of the liquid in the chamber into respective alignment with the plurality of openings. The controller may be further configured to control the electric field so as to alter the wettability of at least one surface portion in contact with the liquid in the chamber. In another aspect, the controller may be configured to control the electric field so as to selectively alter the at least one surface portion between exhibiting hydrophobic characteristics and hydrophilic characteristics. The controller may be configured to selectively alter the electric potential of the first and second substrates.

One or both of the first and second substrates may comprise a hydrophobic layer facing the chamber.

The device may further comprise a plurality of electrodes associated with the first substrate. The plurality of electrodes may be independently electrically chargeable. The plurality of electrodes may be disposed in an array of rows and columns. The at least one opening may comprise a plurality of openings aligned with at least some of the plurality of electrodes, and the plurality of openings are configured to be respectively aligned with a plurality of wells in a titer plate. The plurality of electrodes may be configured to permit liquid supplied to the chamber to be positioned so as to form a plurality of substantially parallel rows. The device may further comprise at least one additional electrode associated with the second substrate.

The device may further comprise a first substrate comprising a distribution channel configured to receive liquid to be dispensed. The distribution channel may be in flow communication with the plurality of substantially parallel rows.

The device may further comprise an input port in flow communication with the chamber.

In a further exemplary aspect a biological analysis system may comprise a device according to any exemplary aspects described above and a plurality of stations, including at least one liquid storing station configured for storing liquid to be used in a biological analysis procedure. The device may be configured to be movable between the at least one liquid storing station and at least one other station of the plurality of stations.

The various dispensing devices and methods in accordance with aspects of the invention may allow for precise positioning of controlled small volumes (e.g., on the order of microliters or nanoliters) of liquid in order to dispense the small volumes of liquid into specific formats on a testing platform. The various dispensing devices and methods could be controlled via software in order to accommodate desired dispensing operations. Further, it is envisioned that the dispensing devices and methods disclosed herein could be produced in a cost-efficient manner, for example, by employing foundry services.

It is also envisioned that the exemplary devices and methods according to the invention could be used to perform multi-plexing procedures. For example, the devices could be provided with a plurality of input ports in which differing liquids could be input into the device along separated rows and/or columns of electrodes. By selectively activating electrodes, the input liquids could be kept segregated or combined together as desired, and moved along the dispensing devices as desired. Reference is made to U.S. Publication No. 2003/0205632, incorporated by reference herein, for an exemplary method of how electrowetting principles can be utilized to perform multi-plexing procedures.

It should be understood that the particular electrode array that is utilized with the dispensing devices and methods described herein can be selected based on factors such as the desired movement of liquid through the dispensing device, the desired positioning of the individual portions of liquid to be dispensed, the desired amount of liquid in each individual portion which is to be dispensed, and other similar factors.

It should be noted that sizes and configurations of various structural parts and materials used to make the above-mentioned parts are illustrative and exemplary only. One of ordinary skill in the art would recognize that those sizes, configurations, and materials can be changed to produce different effects or desired characteristics. By way of example, it is envisioned that by utilizing lithographic materials and processes capable of micrometer sized features, the various dispensing devices and methods according to aspects of the invention may be scaled to accommodate various volumes of liquids and portion densities (e.g., high bandwidth capability of the number of portions of liquid dispensed over a given area) as desired.

In this application, the use of the singular includes the plural unless specifically stated otherwise. It is noted that, as used in this specification and the appended claims, the singular forms "a," "an," and "the," include plural referents unless expressly and unequivocally limited to one referent. In this application, the use of "or" means "and/or" unless stated otherwise. Furthermore, the use of the term "including", as well as other forms, such as "includes" and "included", is not limiting. As used herein, the term "include" and its grammatical variants are intended to be non-limiting, such that recitation of items in a list is not to the exclusion of other like items that can be substituted or added to the listed items. Also, terms such as "element" or "component" encompass both elements and components comprising one unit and elements and components that comprise more than one subunit unless specifically stated otherwise. Wherever possible, the same reference numbers will be used throughout the drawings to refer to the same or like parts.

The section headings used herein are for organizational purposes only and are not to be construed as limiting the described subject matter in any way. All literature and similar materials cited in this application, including patents, patent applications, articles, books, treatises, and internet web pages are expressly incorporated by reference in their entirety for any purpose. In the event that one or more of the incorporated literature and similar materials defines or uses a term in such a way that it contradicts that term's definition in this application, this application controls. While the present teachings are described in conjunction with various exemplary embodiments, it is not intended that the present teachings be limited to such embodiments. On the contrary, the present teachings encompass various alternatives, modifications, and equivalents, as will be appreciated by those of skill in the art.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It will be apparent to those skilled in the art that various modifications and variations can be made to the structure and methodology of the present invention. Thus, it should be understood that the invention is not limited to the examples discussed in the specification. Rather, the present invention is intended to cover modifications and variations. Other embodiments of the invention will be apparent to those skilled in the art from consideration of the specification and practice of the invention disclosed herein.

What is claimed is:

1. An electrowetting system, comprising:
   a sample chamber including a substantially planar array of independently addressable electrodes embedded in a first substrate, a conducting electrode embedded in a second substrate proximate to the first substrate, a first insulating layer formed over the addressable electrodes, the second substrate and first substrate defining a volume and a path having a plurality of addressable locations corresponding to each of the plurality of the independently addressable electrodes; and a controller to provide electrical signals to the independently addressable electrodes;

wherein the sample chamber is configured to receive a liquid and engage one or more of the addressable electrodes to partition the liquid into a plurality of droplets, and wherein the sample chamber communicate each of the plurality of droplets to one of a plurality of dispensing through-holes by independently addressing one or more of the addressable electrodes.

2. The electrowetting system of claim 1, wherein the sample chamber is configured to receive discrete quantities of liquid from an external device alignable with an input port of the electrowetting system.

3. The electrowetting system of claim 1, wherein the conducting electrode defines a single electrode.

4. The electrowetting system of claim 1, wherein the controller communicates a signal to one or more electrodes to partition the liquid into droplets and to move the droplets.

5. The electrowetting system of claim 1, wherein the first insulating layer comprises a hydrophobic surface.

6. The electrowetting system of claim 1, wherein the liquid comprises a biological fluid.

7. The electrowetting system of claim 1, wherein the electrodes are arranged in a path to facilitate droplet transportation within the volume.

8. The electrowetting system of claim 1, wherein at least one of the addressable electrodes is made hydrophobic by applying the signal.

9. The electrowetting system of claim 1, wherein the sample holder is configured to receive the liquid from an external device, engage one or more of the addressable electrodes to partition the liquid into a plurality of droplets and to substantially simultaneously communicate each droplet to be dispensed from a respective dispensing through-hole.

10. An electrowetting system, comprising:
a sample holder including a substantially planar array of independently addressable electrodes embedded in a first substrate, a conducting electrode embedded in a second substrate proximate to the first substrate, a first insulating layer formed over the addressable electrodes, the second substrate and the first substrate defining a volume and a path having a plurality of addressable locations corresponding to each of the plurality of the independently addressable electrodes; and
a controller to provide electrical signals to the independently addressable electrodes;
wherein the sample holder is configured to receive a fluid volume and engage the one or more of the addressable electrodes to partition the fluid volume into a plurality of droplets, communicate each of the plurality of droplets to one of a plurality of locations for extraction by independently addressing one or more of the addressable electrodes.

11. The electrowetting system of claim 10, wherein the sample holder further comprises a plurality of output ports.

12. The electrowetting system of claim 10, wherein the sample holder is configured to receive discrete fluid volumes from an external device alignable with an input port of the electrowetting system.

13. The electrowetting system of claim 10, wherein the conducting electrode defines a single electrode.

14. The electrowetting system of claim 10, wherein the controller communicates an electric potential to the one or more electrodes to control partition of the fluid volume and to control movement of the droplets.

15. The electrowetting system of claim 10, wherein the first insulating layer comprises a hydrophobic surface.

16. The electrowetting system of claim 10, wherein the fluid volume comprises an immiscible droplet.

17. An electrowetting apparatus, comprising:
one or more input ports to receive one or more input reagents;
a first substrate supporting an array of one or more primary electrodes;
a second substrate supporting a secondary electrode;
a volume substantially situated between the first substrate and the second substrate, the volume comprising a plurality of addressable regions, each addressable region defined by electrical charge communication between one of the primary electrodes and the secondary electrode;
a plurality of output ports to fluidly communicate with the volume, the plurality of output ports arranged to receive a fluidic mixture of the input reagents;
wherein one or more of the primary electrodes of the array is configured to be actuated to facilitate passage of a first quantity of the fluidic mixture through the volume and to meter a second quantity of the fluidic mixture to each of the respective ones of the output ports.

18. The apparatus of claim 17, wherein at least one the output port is a reservoir.

19. The apparatus of claim 17, wherein the first quantity is substantially similar to the second quantity.

20. The apparatus of claim 17, wherein the first quantity is larger than the second quantity.

* * * * *